(12) United States Patent
Allemandi et al.

(10) Patent No.: US 10,993,994 B2
(45) Date of Patent: May 4, 2021

(54) ALBUMIN NANOPARTICLES FOR THE TREATMENT OF CANCER AND OCULAR DISEASES

(71) Applicants: UNIVERSIDAD DE NAVARRA, Navarra (ES); CONSEJO NACIONAL DE INVESTIGACIONES CIENTÍFCAS Y TÉCNICAS, Ciudad Autónoma de Buenos Aires (AR); UNIVERSIDAD NACIONAL DE CÓRDOBA, Córdoba (AR)

(72) Inventors: Daniel Alberto Allemandi, Córdoba (AR); Carolina Boiero, Córdoba (AR); Juan Manuel Irache Garreta, Navarra (ES); Juan Manuel Llabot, Cordova (ES); Inés Luis De Redíin Subirá, Navarra (ES); Iván Peñuelas Sánchez, Navarra (ES); Gemma Quincoces Fernández, Navarra (ES)

(73) Assignees: UNIVERSIDAD NACIONAL DE CÓRDOBA, Cordoba (AR); CONSEJO NACIONAL DE INVESTIGACIONES CIENTÍFICAS Y TÉCNICAS, Cuidad Autónoma de Buenos Aires (AR); UNIVERSIDAD DE NAVARRA, Navarra (ES)

( * ) Notice: Subject to any disclaimer, the term of this patent is extended or adjusted under 35 U.S.C. 154(b) by 0 days.

(21) Appl. No.: 16/625,040

(22) PCT Filed: Jun. 21, 2018

(86) PCT No.: PCT/EP2018/066639
§ 371 (c)(1),
(2) Date: Dec. 20, 2019

(87) PCT Pub. No.: WO2018/234489
PCT Pub. Date: Dec. 27, 2018

(65) Prior Publication Data
US 2020/0138914 A1    May 7, 2020

(30) Foreign Application Priority Data
Jun. 21, 2017 (EP) ..................... 17382383

(51) Int. Cl.
```
A61K 38/38     (2006.01)
A61P 35/00     (2006.01)
A61K 9/00      (2006.01)
A61K 9/51      (2006.01)
A61K 39/395    (2006.01)
A61K 47/38     (2006.01)
A61K 39/00     (2006.01)
```
(52) U.S. Cl.
CPC .......... *A61K 38/385* (2013.01); *A61K 9/0048* (2013.01); *A61K 9/51* (2013.01); *A61K 39/3955* (2013.01); *A61K 47/38* (2013.01); *A61P 35/00* (2018.01); *A61K 2039/505* (2013.01)

(58) Field of Classification Search
None
See application file for complete search history.

(56) References Cited

U.S. PATENT DOCUMENTS

| 2011/0104069 A1 | 5/2011 | Xu et al. |
| 2016/0095942 A1 | 4/2016 | Markovic et al. |
| 2016/0317460 A1 | 11/2016 | Benita et al. |

FOREIGN PATENT DOCUMENTS

| WO | 2011053803 A2 | 5/2011 |
| WO | 2013042125 A2 | 3/2013 |

OTHER PUBLICATIONS

International Search Report, dated Oct. 9, 2018 for International Application No. PCT/EP2018/066639.
Hao et al., "Preparation and Characterization of Bevacizumab (Avastin) Nanoparticles for the Treatment of Age Related Macular Degeneration", American Association of Pharmaceutical Scientists (AAPS) Annual Meeting and Exposition, Los Angeles, California, Nov. 2009.
Li, F. et al., "Controlled Release of Bevacizumab Through Nanospheres for Extended Treatment of Age-Related Macular Degeneration", The Open Ophthalmology Journal, 2012, 6, 54-58.
Pan CK et al., "Comparison of Long-Acting Bevacizumab Formulations in the Treatment of Choroidal Neovascularization in a Rat Model", J. Ocul. Pharmacol. Ther., 2011, 27(3), 219-224.
Varshochian Reyhaneh et al., "The protective effect of albumin on bevacizumab activity and stability in PLGA nanoparticles intended for retinal and choroidal neovascularization treatments", European Journal of Pharmaceutical Sciences, 2013 50(3-4), 341-352.
Elzoghby et al., "Albumin-based nanoparticles as potential controlled release drug delivery systems", Journal of Controlled Release, 2012, 157(2), 168-182.
Lohcharoenkal, W. et al., "Protein Nanoparticles as Drug Delivery Carriers for Cancer Therapy", BioMed Research International, 2014.
Llabot et al., "Preparation of Human Serum Albumin (HSA) nanoparticles Stabilized by Polymer Coating for the treatment of corneal neovascularization", 19th International Symposium on Microencapsulation, 2013.
Wang G. et al., "Preparation of BMP-2 Containing Bovine Serum Albumin (BSA) Nanoparticles Stabilized by Polymer Coating", Pharmaceutical Research, 2008, 25(12), 2896-2909.
Gao Y., et al., "In Vitro Release Kinetics of Antituberculosis Drugs from Nanoparticles Assessed Using a Modified Dissolution Apparatus", Biomed Research International, 2013.

(Continued)

*Primary Examiner* — Robert A Wax
*Assistant Examiner* — Quanglong N Truong
(74) *Attorney, Agent, or Firm* — Tristan A. Fuierer; Olive Law Group, PLLC

(57) ABSTRACT

The present invention refers to nanoparticles comprising a core, said core comprising a non-crosslinked albumin matrix and a monoclonal antibody, optionally coated with a non-ionic polymer for use as a medicament, to a pharmaceutical composition comprising said nanoparticles, as well as their use in the treatment of cancer an ocular diseases.

19 Claims, 13 Drawing Sheets

(56) References Cited

OTHER PUBLICATIONS

Rodrigues E.B. et al, "Therapeutic monoclonal antibodies in ophthalmology," Progress in retinal and eye research, 2009, 28(2), 117-144.

Wang W. et al., "Antibody Structure, Instability, and Formulation", Journal of Pharmaceutical Sciences, 2007, 96(1), 1-26.

Prica, A. et al.; "Rituximab in Lymphoma and Chronic Lymphocytic Leukaemia: A Practice Guideline," Clinical Oncology, 2016, pp. 1-16.

Blick, Stephanie K.A., et al.; "Cetuximab: A Review of its Use in Squamous Cell Carcinoma of the Head and Neck and Metastatic Colorectal Cancer," Drugs, 2007, vol. 67, pp. 2585-2607.

1

ALBUMIN NANOPARTICLES FOR THE TREATMENT OF CANCER AND OCULAR DISEASES

CROSS-REFERENCE TO RELATED APPLICATIONS

This application is filed under the provisions of 35 U.S.C. § 371 and claims the priority of International Patent Application No. PCT/EP2018/066639 filed on Jun. 21, 2018 entitled "ALBUMIN NANOPARTICLES FOR THE TREATMENT OF CANCER AND OCULAR DISEASES" in the name of Daniel Alberto ALLEMANDI, et al., which claims priority to European Patent Application No. 17382383.2, filed on Jun. 21, 2017, both of which are hereby incorporated by reference herein in their entirety.

FIELD OF THE INVENTION

The present invention refers to nano-sized drug delivery systems, and more particularly to nanoparticles containing a matrix of albumin and a monoclonal antibody, to be used in the treatment of cancer and ocular diseases.

BACKGROUND

Monoclonal antibodies have emerged as an interesting group of glycoproteins to be used in different therapeutic areas, such as cancer, autoimmune and chronic inflammatory diseases and the treatment of transplant rejection. At present, there are, approximately, 30 monoclonal antibodies approved by the Regulatory Agencies (FDA & EMEA).

One of these monoclonal antibodies is Bevacizumab, an immunoglobulin G (IgG) that targets VEGF-A (vascular endothelial growth factor) and includes four of the major isoforms of VEGF. It was approved by the FDA in 2004 for first-line treatment of metastatic colorectal cancer and afterwards was also approved for other cancers, like non-small-cell lung cancer or metastatic breast cancer. Recently, bevacizumab has started to be used in the treatment of eye diseases including corneal or retinal neovascularization, diabetic retinopathy and age-related macular degeneration.

Topical application on to the eye's surface is a common route for drugs administration. However, the protective mechanisms (slinking, lachrymation and drainage) decrease the bioavailability of drug by removing rapidly the formulation. In the past few years, intravitreal injection of Bevacizumab has been found to be a very efficient treatment for the wet form of age-related macular degeneration, proliferative diabetic retinopathy and choroidal neovascularization. Short terms results suggested that intravitreal bevacizumab was well tolerated and associated with improvement in visual acuity, decreased retinal thickness and reduction in angiographic leakage in most patients. However, to achieve and maintain the improvement in vision, repetitive injection and follow-up visits are required. This entails a high risk of complications such as endophthalmitis, as well as repetitive pain, apprehension and distress associated with inserting needles into the eyes. Moreover, the intravitreal half-life of injected bevacizumab is approximately only 3 days.

In the case of cancer therapies, current treatments strategies usually involve intrusive processes including the application of catheters for chemotherapy to shrink the tumor prior to their removal by surgery. Research efforts to improve the effectiveness of cancer therapy have led to a substantial improvement in patient survival, however, problems associated with toxic side effects and poor quality of life in patients remain a major issue.

Therefore, an effective drug delivery method needs to be developed to render bevacizumab, as well as other monoclonal antibodies, delivery less invasive and long-lasting for the treatment of cancer and ocular diseases.

In this sense, nanoparticles have emerged as a suitable vehicle for drugs administration and have yielded promising results in ophthalmic field as well as in cancer therapies. There are a large variety of materials that can be used for preparing such nano-sized delivery systems. For example, monoclonal antibody bevacizumab has been incorporated in nanoparticles of PLGA for the treatment of age-related macular degeneration [Hao et al., *American Association of Pharmaceutical Scientists (AASP) Annual Meeting and Exposition*, Los Angeles, Calif., November 2009; Li, F. et al., *The Open Ophthalmology Journal*, 2012, 6, 54-58], as well as for retinal and choroidal neovascularization treatments [Pan C K et al., *J Ocul. Pharmacol. Ther.*, 2011, 27(3), 219-224; Varshochian, R. et al., *European Journal of Pharmaceutical Sciences*, 2013, 50, 341-352].

However, natural biopolymers are preferred over synthetic materials. In this regard, human serum albumin has been widely used to prepare nanoparticles for drug delivery due to the fact that they are biocompatible, biodegradable, non-toxic and non-immunogenic. Albumin nanoparticles have gained considerable attention owing to their high binding capacity of various drugs and being well tolerated without any serious side-effects.

In the last years, a great variety of physico-chemical processes for the preparation of albumin nanoparticles have been proposed, including thermal gelation, emulsification and desolvation (coacervation). In any case, the desolvation based-procedures appear to be the most popular due to their simplicity and repeatability. However, the just obtained nanoparticles are unstable and a supplementary step of physical, chemical or enzymatic stabilization has to be performed in order to prolong their half-life in aqueous environment and/or prevent from the formation of macro-aggregates of the protein.

In general, cross-linkage of the albumin is one of the most popular strategies for the stabilization of albumin nanoparticles. Elzoghby et al. [*Journal of Controlled Release*, 2012, 157, 168-182] compiles different methods for preparing albumin nanoparticles and their use as active drug delivery systems. Particular mention is made about the instability of nanoparticles in aqueous media which require them to be crosslinked, citing glutaraldehyde as the common chemical cross-linking agent used in the art. Lohcharoenkal, W. et al. [*BioMed Research International*, 2014] also refers to the instability of albumin nanoparticles as they dissolve or coalesce to form a separate phase if not cross-linked. Llabot et al. [19$^{th}$ *International Symposium on Microencapsulation*, 2013] describes albumin nanoparticles cross-linked with Gantrez which encapsulates bevacizumab, as well as their use in corneal vascularization.

Thus, cross-linking stabilizes albumin nanoparticles and reduces the enzymatic degradation as well as the delivery of the active ingredient from the nanoparticle.

However, while glutaraldehyde is highly effective for stabilizing the nanoparticles, its use is questionable due mainly to its toxicity which hampers its use for in vivo delivery. Thus, it is essential to remove the cross-linker as completely as possible. Furthermore, glutaraldehyde can affect the stability of biomacromolecules, more particularly protein drugs, antibodies and peptides, in the nanoparticles since it reacts with functional groups present in the macromolecules (such as primary amine residues), resulting in an important loss of their activity.

In order to solve this important drawback, different strategies have been proposed to harden or stabilize the just formed albumin nanoparticles without the need of using toxic reagents. Amongst others, the stabilization of nanoparticles can be obtained by thermal treatment, high hydrodynamic pressure or enzymatic cross-linkage with genipin or transglutaminase.

Surface coating has also been used to stabilize albumin nanoparticles. For example, cationic polymers, such as polylysine or polyethyleneimine, have been used to coat bovine serum albumin nanoparticles to improve their stability [Wang et al., *Pharm. Res.*, 2008, 25(12), 2896-2909].

WO2013/042125 describes the preparation of glutaraldehyde crosslinked bovine serum albumin nanospheres incorporating bevacizumab and the subsequent encapsulation of said nanospheres in a cover of ionic PLGA.

WO2011/053803 also refers to nanoparticles having a polymeric shell encapsulating a therapeutic agent, such as bevacizumab, for treating ocular diseases.

In view of all above, adequate delivery systems that preserve the integrity and activity of monoclonal antibodies and control its release from nanoparticles are required.

BRIEF DESCRIPTION OF THE INVENTION

The authors of the present invention have found that the entrapment of a monoclonal antibody, such as bevacizumab, in a matrix of albumin provides nanoparticles with a high stability in aqueous solution and, surprisingly, said nanoparticles do not need to be cross-linked or stabilized by other means, thus allowing the maintenance of the 3D structure as well as the biological activity of the antibody once it is delivered. On the contrary, and as shown in the experimental part below, the use of glutaraldehyde (the most common cross-linker used in the prior art to stabilize nanoparticles of albumin) inactivates the antibody, thus making unfeasible the use of cross-linked nanoparticles for the encapsulation of these kind of active ingredients.

The authors have also tested non-cross-linked nanoparticles decorated with non-ionic polymers, such hydroxypropyl methyl cellulose phthalate (HPMC-P) and polyethyleneglycol 35,000 (PEG35), as well as Eudragit® S-100 (poly(methacrylic acid, methyl methacrylate) 1:2) and observed that the integrity of the antibody is also maintained.

In addition to that, following the method described herein below, the monoclonal-loaded albumin nanoparticles can be manufactured as a dry powder ready to disperse and reconstitute by the simple addition of water or an aqueous solution.

Furthermore, the nanoparticles of the invention allow a sustained release of the monoclonal antibody and constitute a drug delivery system of great interest for in vivo applications as pointed out by the obtained biological activity data in a corneal neovascularization animal model.

Also, the biodistribution assays carried out with albumin nanoparticles coated with non-ionic polymers point out that they are able to concentrate in tumor tissues, thus making them very promising nanoparticulate systems for releasing the monoclonal antibody into those affected tissues.

In fact, in vivo experiments have shown that nanoparticles of the invention are able to release the monoclonal antibody in the tumor tissue since lower concentration of said antibody are present in serum when compared to the administration of the same monoclonal antibody in aqueous solution. Furthermore, the volume of the tumor is significantly reduced.

Thus, a first aspect of the present invention refers to a nanoparticle for use in medicine, wherein said nanoparticle comprises a solid core, said solid core comprising a non-crosslinked albumin matrix and a monoclonal antibody and wherein the monoclonal antibody is distributed throughout the albumin matrix, said solid core being optionally coated with a non-ionic polymer.

A second aspect of the invention refers to a pharmaceutical composition comprising:
  a plurality of nanoparticles, said nanoparticles comprising a solid core, said solid core comprising a non-crosslinked albumin matrix and a monoclonal antibody and wherein the monoclonal antibody is distributed throughout the albumin matrix, said solid core being optionally coated with a non-ionic polymer; and
  an excipient, carrier or vehicle pharmaceutically acceptable.

In another aspect, the invention relates to said pharmaceutical composition of the invention for use in medicine.

A further aspect of the invention is a nanoparticle for use in the treatment of ocular diseases, wherein said nanoparticle comprises a solid core, said solid core comprising a non-crosslinked albumin matrix and a monoclonal antibody and wherein the monoclonal antibody is distributed throughout the albumin matrix, said solid core being optionally coated with a non-ionic polymer.

Another aspect of the invention is a nanoparticle for use in the treatment of cancer, wherein said nanoparticle comprises a solid core, said solid core comprising a non-crosslinked albumin matrix and a monoclonal antibody and wherein the monoclonal antibody is distributed throughout the albumin matrix, said solid core being optionally coated with a non-ionic polymer.

Finally, another aspect of the invention relates to a nanoparticle comprising a solid core, said solid core comprising a non-crosslinked albumin matrix and a monoclonal antibody and wherein the monoclonal antibody is distributed throughout the albumin matrix, said solid core being coated with a non-ionic polymer.

***p<0.005 ANOVA followed by Tukey test significantly different from B-NP

Figure 18:
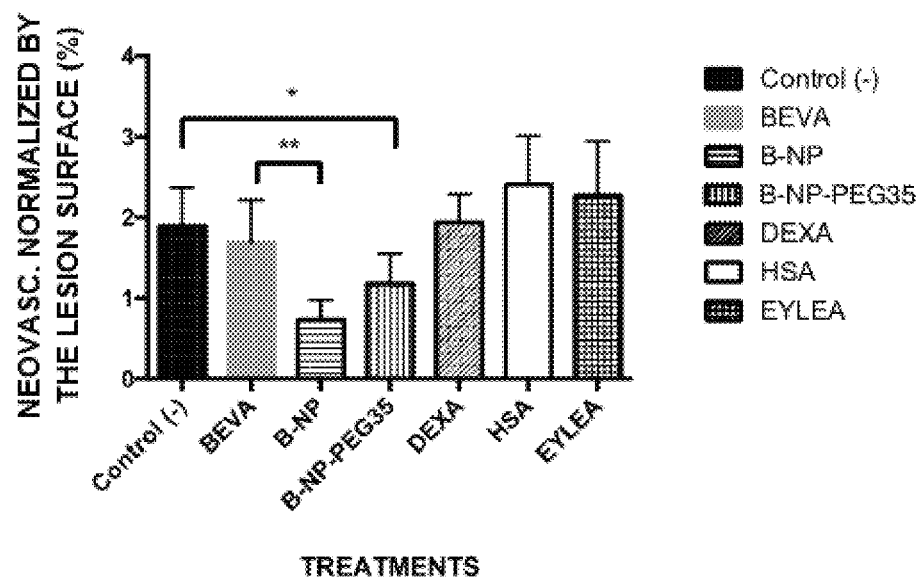

FIG. 18. Neovascularization area normalized by the lesion. The data are shown as the mean±SD (n=9).
*p<0.01 ANOVA followed by Tukey test significantly different from Control (−)
**p<0.005 ANOVA followed by Tukey test significantly different from BEVA FIG. 19. Photomicrographs of corneal sections of normal and neovascularized corneas treated with bevacizumab. (e, epithelial layer; s, stroma; ac, anterior chamber; v, stromal microvessels). A) A photomicrograph of rat normal cornea showing intact epithelium (e), the stroma containing regular parallel collagen lamellae with flattened keratocytes in between; B) A photomicrograph of rat cornea from group treated with albumin nanoparticles loaded with bevacizumab (B-NP). Thickness of the cornea within normal limits, intact epithelium and stroma slightly disorganized and lax with a very discreet infiltration. C) Photomicrographs of rat cornea from group treated with albumin nanoparticles loaded with bevacizumab and coated with PEG35 (B-NP-PEG35). Normal epithelium, numerous stromal microvessels (v). Corneal thickness within normal values; D & E): Photomicrographs of rat cornea from group treated with bevacizumab. Epithelium preserved and hypertrophic that separates from the stroma. Thickening of the stroma with numerous and desorganized fibroblast, intense cellular infiltration and edema (*); F) Photomicrograph of rat cornea from group treated with Physiological Serum. Serious alterations within the cornea, central erosion with and increase of the thickness. Intense fibrosis with large disorganized fibroblast, moderate inflammatory infiltration and neovascularization (v). Formation of a cyst (c) from epithelium cells that shows an attempt to abnormal repair. Scale bar, 200 μm, H.E. X100.

Figure 20:
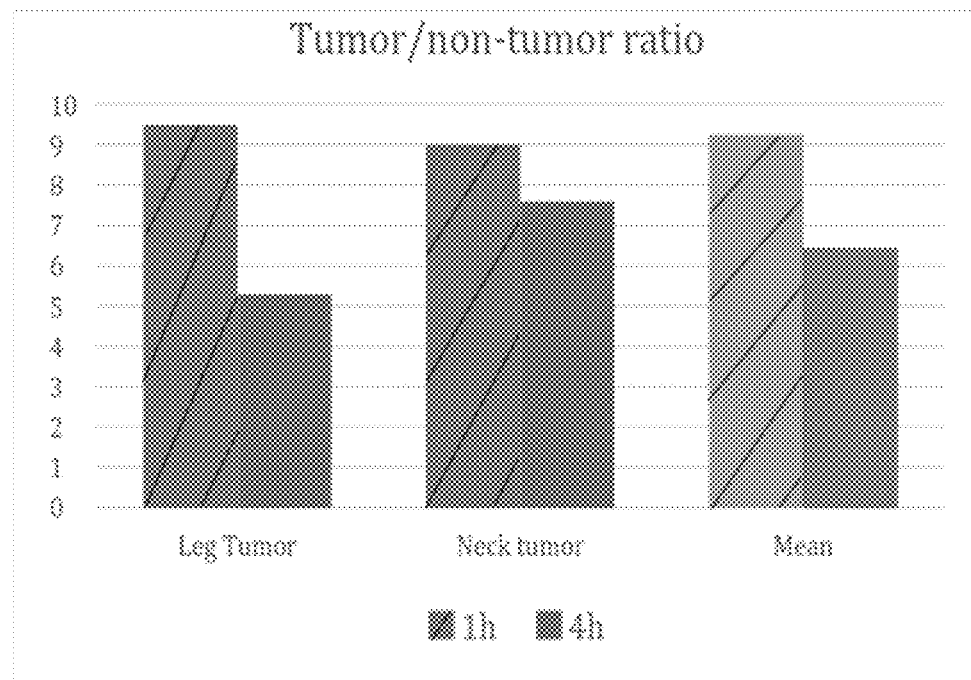

FIG. 20. Tumour to non-tumour ratios for the leg and neck tumours in animals treated with albumin nanoparticles coated with PEG35 (NP-PEG35). Values correspond to the mean value from three animals obtained 1 hour (blue bars) and 4 hours (red bars) after intravenous (i.v.) administration of radiolabelled nanoparticles.

Figure 21:
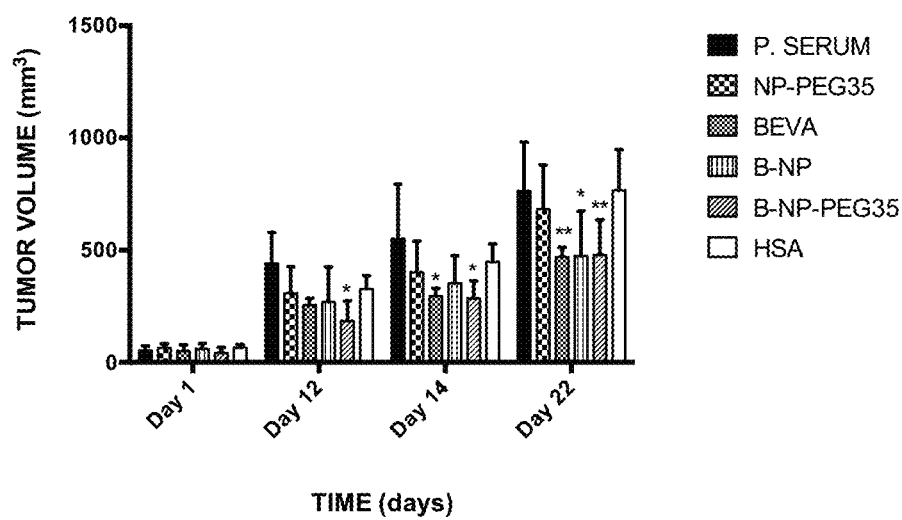

FIG. 21. Tumor volume (mm$^3$). The data are shown as the mean+SD (n≥6).
*p<0.05 ANOVA followed by Tukey test significantly different from physiological serum.
**p<0.01 ANOVA followed by Tukey test significantly different from physiological serum.

Figure 22:
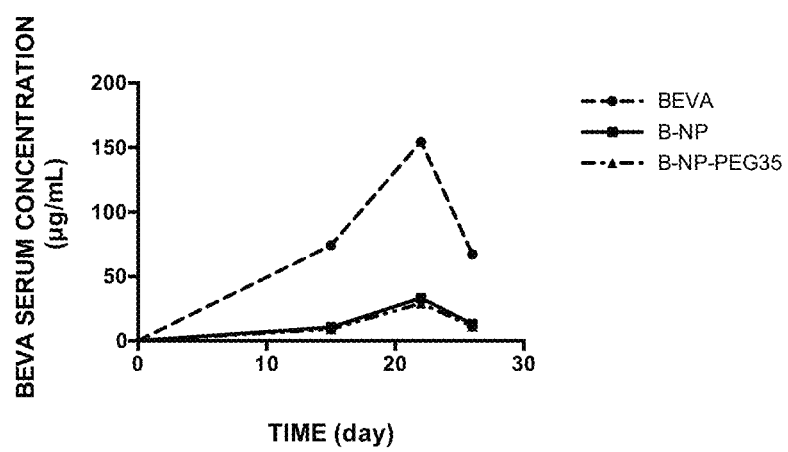

FIG. 22. Bevacizumab serum concentration (μg/mL) versus time (day).

DETAILED DESCRIPTION OF THE INVENTION

As mentioned before, a first aspect of the present invention refers to a nanoparticle for use in medicine, wherein said nanoparticle comprises a solid core, said solid core comprising a non-cross-linked albumin matrix and a monoclonal antibody and wherein the monoclonal antibody is distributed throughout the albumin matrix, said solid core being optionally coated with a non-ionic polymer.

In a particular embodiment, the present invention refers to a nanoparticle for use in medicine, wherein said nanoparticle comprises a solid core, said solid core consisting of a non-cross-linked albumin matrix and a monoclonal antibody, and wherein the monoclonal antibody is distributed throughout the albumin matrix, said solid core being optionally coated with a non-ionic polymer.

In another particular embodiment, the present invention refers to a nanoparticle for use in medicine, wherein said nanoparticle consists of a solid core, said solid core comprising a non-cross-linked albumin matrix and a monoclonal antibody, and wherein the monoclonal antibody is distributed throughout the albumin matrix, said solid core being optionally coated with a non-ionic polymer.

In another particular embodiment, the present invention refers to a nanoparticle for use in medicine, wherein said nanoparticle consists of a solid core, said solid core consisting of a non-cross-linked albumin matrix and a monoclonal antibody, and wherein the monoclonal antibody is distributed throughout the albumin matrix, said solid core being optionally coated with a non-ionic polymer.

As used herein, the term "nanoparticle" refers to a colloidal system having spherical or quasi-spherical shape and having a mean size less than 1 μm. In a particular embodiment, the nanoparticle has a mean size ranging from 100 to 900 nm, more preferably from 150 to 800 nm, even more preferably from 200 to 500 nm, and much more preferably from 200 to 400 nm.

"Mean size" is understood as the average diameter of the nanoparticle population, moving together in an aqueous medium. The mean size of these systems can be measured by standard methods known by the person skilled in the art and are described, for example, in the experimental part below.

In the context of the present invention, the term nanoparticle refers to a nanosphere or to a decorated nanosphere.

By "nanosphere" should be understood a solid non-crosslinked matrix of albumin or a continuous material of albumin wherein the monoclonal antibody is distributed throughout said matrix, thus not featuring a distinct core/shell structure.

By "decorated nanosphere" should be understood a nanosphere as defined above, wherein the solid non-crosslinked matrix of albumin is coated or decorated with a non-ionic polymer.

Accordingly, the nanoparticles of the invention are absent of any other polymeric coating which is not a non-ionic polymer.

In a preferred embodiment, the nanoparticle of the invention is a nanoparticle wherein when the solid core is coated, the nanoparticle is absent of any other polymeric coating which is not a non-ionic polymer. Although the nanoparticles of the invention do not require a coating polymer, the inventors have found that when the nanoparticle is absent of any other polymeric coating which is not a non-ionic polymer, said particles display an advantageous effect over the same particles when an ionic coating is used. For example, when the nanoparticle of the invention is coated with an ionic polymer, the particles show a very fast release profile of the antibody (burst release).

Thus, when nanoparticles used in the invention are not coated with a non-ionic polymer said nanoparticles should be considered as nanospheres according to the definition given above, whereas when nanoparticles used in the invention are coated with a non-ionic polymer said nanoparticles should be considered as decorated nanospheres according also to the definition given above.

In contrast to the nanoparticles used in the prior art where the albumin matrix is cross-linked or stabilized by other means, the nanoparticles used in the invention are characterized for having a solid core of a non-crosslinked matrix of albumin, understanding as such an organized structure or pattern resulting from the local interactions between albumin and monoclonal antibody. Thus, in the scope of the present invention, nanoparticles are forming solid matrix systems.

Therefore, the term "solid core" refers to a solid non-crosslinked matrix-type structure in which the albumin forms a continuous structure where the monoclonal antibody is distributed, preferably homogeneously distributed, throughout the entire matrix.

Thus, the solid core of the nanoparticles used in the invention has not differentiated external and internal structures and, therefore, the monoclonal antibody is distributed, more preferably homogeneously distributed, within the entire matrix of albumin but not encapsulated or confined within a central cavity thereof.

In a particular embodiment, the nanoparticle used in the invention is a nanosphere as defined above. More particularly, in said nanoparticles the solid core is not coated with a non-ionic polymer. As described throughout the text, and also shown in the examples the nanoparticles of the invention are stable and do not require any encapsulation. In the context of the present invention, the term "stable" refers to the increase in the stability of the particles such that the particles can be used in medicine, without any disaggregation of the material. Thus, in a particular embodiment, the nanoparticle of the present invention is a stable nanoparticle, with or without the presence of an optional coating polymer.

In another particular embodiment, the nanoparticle used in the invention is a decorated nanosphere as defined above, i.e., comprises or consists of a solid core of a solid matrix of albumin or a continuous material of albumin wherein the monoclonal antibody is distributed throughout said matrix, and wherein the solid core is coated with a non-ionic polymer.

In fact, an additional aspect of the invention relates to a nanoparticle comprising a solid core, said solid core comprising a non-crosslinked albumin matrix and a monoclonal antibody and wherein the monoclonal antibody is distributed throughout the albumin matrix, said solid core being coated with a non-ionic polymer.

More particularly, the invention also refers to a nanoparticle comprising a solid core, said solid core consisting of a non-crosslinked albumin matrix and a monoclonal antibody and wherein the monoclonal antibody is distributed throughout the albumin matrix, said solid core being coated with a non-ionic polymer.

Also particularly, the invention refers to a nanoparticle consisting of a solid core, said solid core comprising a non-crosslinked albumin matrix and a monoclonal antibody and wherein the monoclonal antibody is distributed throughout the albumin matrix, said solid core being coated with a non-ionic polymer.

Even more particularly, the invention also refers to a nanoparticle consisting of a solid core, said solid core consisting of a non-crosslinked albumin matrix and a monoclonal antibody and wherein the monoclonal antibody is distributed throughout the albumin matrix, said solid core being coated with a non-ionic polymer Albumin As used herein, the term "albumin" refers to a family of globular negatively charged proteins, the most common of which are the serum albumins. All the proteins of the albumin family are water-soluble, moderately soluble in concentrated salt solutions, and experience heat denaturation. Albumins are commonly found in blood plasma and differ from other blood proteins in that they are not glycosylated.

The general structure of albumin is characterized by several long a helices allowing it to maintain a relatively static shape, which is essential for regulating blood pressure.

In a particular embodiment, the albumin is a serum albumin. Serum albumin is produced in the liver and dissolved in blood plasma, being the most abundant protein in mammals.

More preferably, the serum albumin is human serum albumin (HSA) or bovine serum albumin (BSA), even more preferably the serum albumin is human serum albumin.

Human serum albumin is encoded by the ALB gene, whereas other mammalian forms, such as bovine serum albumin, are chemically similar.

Human serum albumin has a molecular weight of approximately 65.000 Da and consists of 585 amino acids. The amino acid sequence of HSA contains a total of 17 disulphide bridges, one free thiol (Cys34), and a single tryptophan (Trp214).

Monoclonal Antibody

The term "monoclonal antibody" (mAb or moAb), as used herein, refers to an antibody or antibody fragment produced by a single clone of B-lymphocytes or by a single cell called hybridoma that secrets only one type of antibody molecule. Monoclonal antibodies are produced by methods known to those skill in the art, for instance by making hybrid antibody-forming cells from a fusion of an antibody-producing cell and a myeloma or other self-penetrating cell line.

Monoclonal antibodies have monovalent affinity, in that they bind to the same epitope (the part of an antigen that is recognized by the antibody). Given almost any substance, it is possible to produce monoclonal antibodies that specifically bind to that substance.

For the purpose of the present invention, the monoclonal antibody to be incorporated in the albumin matrix of the nanoparticle should have an affinity for at least one target within the ocular tissue or within a cancerous tissue, or should have an affinity for the tissue itself. For example, the target may be a receptor associated with an ocular disorder or with cancer or a protein associated with an ocular disorder or cancer.

In a particular embodiment, the monoclonal antibody is selected from bevacizumab (Avastin®) which inhibits the function of a natural protein called "vascular endothelial growth factor" (VEGF) that stimulates new blood vessel formation; ranibizumab (Lucentis®) which provides strong binding to VEGF-A; trastuzumab (Herceptin®) which recognizes HER-2 receptor overexpressed in solid tumors; cetuximab (Erbitux®) which recognizes EGFR receptors and rituximab (Mabthera®) which recognizes CD20.

In a preferred embodiment, one or more anti-VEGF antibodies (or fragment thereof) are selected to be incorporated in the albumin matrix, thereby allowing targeting of vascular endothelial growth factor (VEGF) itself. Thus, in a preferred embodiment, the monoclonal antibody is selected from bevacizumab and ranibizumab, more preferably is bevacizumab.

In another preferred embodiment, one or more anti-VEGF R2 antibodies (or fragment thereof) are selected to be incorporated in the albumin matrix, thereby allowing targeting of cells, such as retina pigment epithelial cells, expressing vascular endothelial growth factor receptor 2 (VEGF R2). Examples of anti-VEGF R2 monoclonal antibodies include, but are not limited to, mAb clone Avas12a1 and mAb 2C3.

Over-expression of VEGF and VEGFR2 receptor by epithelial cells, such as retina pigment epithelial cells, is associated, for example, with age-related macular degeneration (AMD).

In another preferred embodiment, the monoclonal antibody is an ocular targeting agent, i.e., an antibody specific for an antigen produced by or associated with ocular tissue implicated in an ocular disorder.

In a particular embodiment, the monoclonal antibody/albumin weight ratio ranges from 0.01 to 0.5, more preferably from 0.01 to 0.2. It has been observed that nanoparticles having a monoclonal antibody/albumin weight ratio less than 0.01 are not stable with time.

Non-Ionic Polymer

The term "non-ionic polymer", as used herein, refers to a hydrophilic polymer that in the preparative conditions of the nanoparticles does not show a net charge. Furthermore, said non-ionic polymer should be biodegradable, i.e., they degrade during in vivo use, as well as biocompatible, i.e., substantially non-toxic or lacking injurious impact on the living tissues or living systems to which they come in contact with.

Examples of suitable non-ionic polymers for use in the present invention are polyvinylalcohol; polyvinylpyrrolidone; polyallylalcohol; polyvinyl methyl ether; polyvinyl acetal; polyalkylene alcohol; a polysaccharide optionally substituted with at least one alkyl group, hydroxyalkyl group, alkoxyalkyl group, or a combination of two or more such groups; polyesters; polyamides, polyurethanes and polyethers.

Preferred polysaccharides include, without limitation, xanthan gums, guar gums, starches, cellulose, dextran and a combination of two or more of the foregoing.

Starches include, for example, corn starch and hydroxypropyl starch.

Cellulose includes, for example, alkyl celluloses, such as $C_1$-$C_6$-alkylcelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcellulose.

In a particular embodiment, the non-ionic polymer is selected from a polysaccharide, polyvinylpyrrolidone, a polyester and a polyalkylene glycol. Preferably, the non-ionic polymer is a water-soluble cellulose selected from hydroxyethylcellulose, hydroxy-n-propylcellulose, hydroxy-n-butylcellulose, hydroxypropylmethyl cellulose, hydroxypropylmethyl cellulose phthalate, and ethylhydroxyethylcellulose; starch; dextran; a polyester selected from compounds under the tradename Eudragit; or a polyalkylene glycol, such as polyethylene glycol or polypropylene glycol.

In another particular embodiment, the non-ionic polymer is selected from hydroxypropylmethylcellulose, hydroxypropylmethyl cellulose phthalate, starch, dextran 70, Eudragit® NM (poly(ethyl acrylate, methyl methacrylate) 2:1); Eudragit® NE (poly(ethyl acrylate, methyl methacrylate) 2:1), polyvinyl pyrrolidone (PVP) and polyethylene glycol (PEG). The polyethylene glycol is preferably PEG-10,000, PEG-20,000 or PEG-35,000 according to the molecular weight thereof.

Preferably the non-ionic polymer is selected from hydroxypropylmethylcellulose, hydroxypropylmethyl cellulose phthalate and PEG 35,000. More preferably, the non-ionic polymer is selected from hydroxypropylmethyl cellulose phthalate and PEG 35,000. Even more preferably, the non-ionic polymer is PEG 35,000.

The non-ionic polymer acts as a coating of the albumin nanoparticles, conferring more stability and, in general, allows increasing the amount of monoclonal antibody to be loaded in the nanoparticle. It has been shown that the presence of the coating does not affect significantly the physical properties of the nanoparticle. Only depending on the nature of the coating, the size and the zeta potential may be slightly increased or decreased.

In a particular embodiment, the non-ionic polymer/albumin ratio ranges from 0.02 to 5 (w/w), more preferably from 0.05 to 2 (w/w).

In another particular and optional embodiment, the nanoparticles used in the present invention further comprise a compound for protecting the albumin matrix during the process of drying the nanoparticles, or of drying the suspension containing the nanoparticles by means of conventional methods, for example, by means of spray drying, hereinafter, "protecting agent". Said protecting agent does not form part of the solid matrix of the nanoparticles but acts as a bulking agent to facilitate the drying of nanoparticles in an efficient way, so as the structure thereof is maintained. Virtually, any compound complying with those characteristics can be used as a protecting agent. In a particular embodiment, said protecting agent is a saccharide.

Non-limiting, illustrative examples of protecting agents which can be used within the context of the present invention include lactose, mannitol, sucrose, maltose, trehalose, maltodextrin, glucose, sorbitol, etc., as well as substances with prebiotic characteristics, such as for example, oligofructose, pectin, inulin, oligosaccharides (e.g. galacto-oligosaccharides, human milk oligosaccharides), lactulose, dietary fiber, etc., and any combination thereof. In a particular embodiment, the protecting agent is selected from lactose, mannitol, sucrose, maltose, trehalose, maltodextrin, glucose, sorbitol and combinations thereof. Preferably, the protecting agent is sucrose. If the nanoparticles used in the invention include a protecting agent, the by weight ratio of the albumin matrix and the protecting agent can vary within a wide range; nevertheless, in a particular embodiment, the albumin:protecting agent by weight ratio is 1:0.1-5, typically 1:0.5-4, preferably about 1:1.

In some embodiments, the nanoparticles used in the invention comprise at least one imaging agent which allows for image-guided targeted delivery of the therapeutic agent by allowing particle location to be imaged before, during or after therapeutic delivery. A variety of imaging agents are suitable for coupling to the surface of the nanoparticle including, but not limited to, fluorescence imaging agents (such as indocyanine green, cyanine 5, cyanine 7, cyanine 9, fluorescein and green fluorescent protein), radionuclide-labeled imaging agents (such as agents comprising iodine-124, $^{99m}$Tc) and magnetic resonance imaging agents (such as gadolinium contrast agents).

The nanoparticles used in the invention may deliver the monoclonal antibody in a controllable process. Such control may allow for delivery of the monoclonal antibody over an extended period of time. For example, it is contemplated that the delivery may occur over a period of from 1 to 30 days. In addition to being adapted to deliver the therapeutic agent in a controllable manner, the nanoparticles may be adapted to provide a variety of options for detection and imaging of the particles before, during and after delivery of the therapeutic agent.

The nanoparticles used in the present invention may optionally comprise a second monoclonal antibody or therapeutic agent in order to also provide a combination therapy.

Said therapeutic agent includes, for example, other proteins such as calcitonin, insulin or cyclosporine A.

The second monoclonal antibody can be any of those mentioned herein above, such as, bevacizumab (Avastin®), ranibizumab (Lucentis®), trastuzumab (Herceptin®), cetuximab (Erbitux®) or rituximab (Mabthera®).

Process for the Preparation of Nanoparticles

The nanoparticles used in the present invention can be prepared by precipitation of the proteins (albumin and monoclonal antibody) in an aqueous environment before purification and drying.

This process comprises:
a) preparing an aqueous solution of albumin and a monoclonal antibody;
b) titrating the aqueous solution of step a) to a pH between 4 and 5;
c) adding a desolvating agent to the aqueous solution of step b).

This method is based on a desolvation process wherein an aqueous solution of albumin and the monoclonal antibody is slowly desolvated by slow addition, such as dropwise addition, of a desolvating agent (typically an organic solvent such as ethanol, acetone or THF), under constant stirring, temperature and pH conditions.

In a particular embodiment, the albumin used in preparing the aqueous solution of step a) is human serum albumin or bovine serum albumin, more preferably is human serum albumin.

In another particular embodiment, the monoclonal antibody used in preparing the aqueous solution of step a) is selected from bevacizumab (Avastin®), ranibizumab (Lucentis®), trastuzumab (Herceptin®), cetuximab (Erbitux®) and rituximab (Mabthera®). More preferably, the monoclonal antibody is bevacizumab or ranibizumab, even more preferably is bevacizumab.

The solution of the albumin and the monoclonal antibody can be prepared by conventional methods known by those skilled in the art, for example by adding the albumin and the monoclonal antibody to the aqueous solution.

The albumin and the monoclonal antibody are preferably mixed at room temperature, i.e., at a temperature comprised between 18° C. and 25° C., preferably between 20° C. and 22° C.

The amount of albumin that can be added to the aqueous solution can vary within a wide range, nevertheless, in a particular embodiment, the amount added to said aqueous solution is comprised between 0.1% and 10% (w/v), preferably between 0.5% and 5% (w/v), even more preferably between 1% and 2% (w/v).

Likewise, the amount of monoclonal antibody that can be added to the aqueous solution can vary within a wide range, nevertheless, in a particular embodiment, the amount added to said aqueous solution is comprised between 0.005% and 1% (w/v), preferably between 0.01% and 0.5% (w/v), even more preferably between 0.01% and 0.4% (w/v).

In a particular embodiment, the albumin and the monoclonal antibody are added to the aqueous solution so as the monoclonal antibody:albumin weight ratio ranges from 0.01 to 0.5, more preferably from 0.01 to 0.2.

In a preferred embodiment, the aqueous solution of the albumin and the monoclonal antibody is subjected to homogenization by means, for example, of stirring.

Step b) of the process for preparing the nanoparticles involves reducing the pH of the aqueous solution containing the albumin and the monoclonal antibody to a slightly acid pH. This allows the precipitation of the nanoparticles in the subsequent step of this process. This can be made by adding an acid component to the aqueous solution obtained after conducting step a), such as HCl 1M.

In a particular embodiment, the aqueous solution is incubated for at least 10 minutes at room temperature.

In step c) of the process for preparing the nanoparticles, a desolvating agent is added to the aqueous solution obtained after conducting step b).

In a preferred embodiment, the addition of the desolvating agent to the aqueous solution obtained after conducting step b) is made under stirring.

In another preferred embodiment said desolvating agent is an organic solvent selected from ethanol and tetrahydrofuran (THF), more preferably is ethanol.

The desolvating agent is slowly added to the aqueous solution under stirring. More preferably, the desolvating agent is dropwise added to the aqueous solution of albumin and monoclonal antibody while stirring the resulting mixture.

In a preferred embodiment, said addition is carried out under an inert atmosphere, such as under nitrogen atmosphere.

After adding the desolvating agent to the aqueous solution of the albumin and monoclonal antibody under the aforementioned conditions, i.e., at room temperature and under stirring, the nanoparticles of the invention are spontaneously formed. In a particular embodiment, said nanoparticles are in suspension in the medium in which they have been obtained.

Thus, the process of the invention allows the formation of a uniform dispersion of nanoparticles by means of simple desolvation process, leading to solid nanospheres having a matrix-type structure wherein the monoclonal antibody is distributed within the whole albumin matrix.

Therefore, the nanoparticles obtained by this process can be considered as self-assembling nanoparticles which are spontaneously formed by means of local interactions between the monoclonal antibody and the albumin upon addition of a desolvating agent.

The process for producing the nanoparticles may comprise an additional step of purifying, for example, by means of filtration techniques, centrifugation or ultracentrifugation.

Likewise, said process may include an additional step of drying the formed nanoparticles in order to obtain the nanoparticles of the invention in the form of a powder. This form of presentation of said nanoparticles contributes to their stability and is further particularly useful for their eventual application in pharmaceutical products.

In a preferred embodiment, the nanoparticles obtained after conducting step c), or after having been purified, are subjected to a drying treatment by conventional methods, for example vacuum drying or, advantageously by means of spray drying or by means of freeze-drying (lyophilization), in order to dry the nanoparticles.

In a particular embodiment, this drying treatment, particularly when it is performed by means of spray drying or by means of lyophilization, comprises adding a protecting agent to the nanoparticles once they are formed. This protecting agent protects the nanoparticle during the drying process thereof, such as for example, a saccharide.

Non-limiting, illustrative examples of saccharides which can be used as protecting agents within the context of the present invention include lactose, mannitol, sucrose, maltose, trehalose, maltodextrin, glucose, etc., as well as polysaccharides with prebiotic characteristics, such as for example, oligofructose, pectin, inulin, oligosaccharides (e.g. galacto-oligosaccharides, human milk oligosaccharides), lactulose, dietary fiber, etc. and mixtures thereof. In a particular embodiment, the protecting agent is selected from lactose, mannitol, sucrose, maltose, trehalose, maltodextrin, glucose, sorbitol and combinations thereof. If the nanoparticles include a protecting agent, this is added in the suitable amount; even though the by weight ratio of the matrix of nanoparticles and the protecting agent can vary within a wide range, in a particular embodiment, the albumin:protecting agent by weight ratio is 1:0.1-5, typically 1:0.5-4, preferably about 1:1.

Nanoparticles can also be dried by means of spray drying. To that end, the suspension containing the nanoparticles and the protecting agent is introduced in a spray-dryer and the processing conditions [air inlet temperature, air outlet temperature, air pressure, sample pumping rate, suction, and airflow] are controlled. The person skilled in the art can set the processing conditions that are most suitable for each case.

This method allows obtaining nanoparticles in the form of a dry powder, which contributes to the stability thereof during long storage periods under controlled or environmental conditions and it can also be easily incorporated in different intended solid and liquid products.

Since the nanoparticles are formed previously to the addition of the protecting agent, this does not form any conjugate or complex with the albumin matrix.

In another particular embodiment, when the nanoparticles to be used in the invention are coated with a non-ionic polymer, said coated nanoparticles may be obtained by incubating the albumin-monoclonal nanoparticles already formed, following the steps a) to c) of the process as defined above, with the non-ionic polymer.

In a particular embodiment, the non-ionic polymer may be any of those described above. Preferably, said non-ionic polymer is selected from hydroxypropylmethylcellulose, hydroxypropylmethyl cellulose phthalate, starch, dextran 70, Eudragit® NM, Eudragit® NE, polyvinyl pyrrolidone and polyethylene glycol (PEG). More preferably the non-ionic polymer is selected from hydroxypropylmethylcellulose, hydroxypropylmethyl cellulose phthalate and PEG 35,000.

In a particular embodiment, the non-ionic polymer/albumin ratio ranges from 0.02 to 5, more preferably from 0.05 to 2.

In another particular embodiment, the incubation of the nanoparticles in the non-ionic polymer is performed during less than 1 hour, more preferably during less than 45 minutes.

Pharmaceutical Composition

The nanoparticles described above have the capacity to entrap a monoclonal antibody and to protect them during processing and storage as well as until its final delivery to the biological site of interest. The deactivation of the monoclonal antibody after incorporation in the different intended products (e.g., pharmaceutical compositions or cosmetic compositions) is thus prevented or substantially reduced. In fact, the experimental tests have pointed out that the monoclonal antibody maintains its integrity in the albumin matrix.

Furthermore, the nanoparticles of the invention allow a sustained release of the monoclonal antibody which also maintains the biological activity in its entirety, thus constituting a drug delivery system of great interest for in vivo applications as pointed out by the biological activity data obtained in a corneal neovascularization animal model. In fact, the in vivo experiments carried out have shown that nanoparticles of albumin and monoclonal antibody provide a significant reduction in the eye surface affected by corneal vascularization when compared to the administration of the same monoclonal antibody in free form.

Moreover, the biodistribution assays carried out with the nanoparticles of the invention point out that they are able to concentrate in tumor tissues, thus making them very promising nanoparticulate systems for releasing the monoclonal antibody into those affected cancerous tissues.

Therefore, in another aspect, the invention relates to a pharmaceutical composition comprising a plurality of nanoparticles as defined above, either in the form of a suspension or in dry powder form, and an excipient, carrier or vehicle pharmaceutically acceptable.

The characteristics of the nanoparticles have already been defined above and are incorporated herein by reference.

In a particular embodiment, the nanoparticles contained in the pharmaceutical composition of the invention are in the form of a dry powder.

While any suitable means of administering the pharmaceutical composition can be used within the context of the present invention, preferably the pharmaceutical composition is administered to the human or animal orally, topically or parenterally, more preferably via intravenous administration, intra-arterial administration, intrapulmonary administration, intra-ocular administration, intramuscular administration, transdermal or subcutaneous administration, oral administration or inhalation.

More preferably, the pharmaceutical composition comprises a vehicle or carrier suitable for oral, topical or parenteral administration.

Based on the particular mode of administration, the pharmaceutical composition may be formulated into tablets, pills, capsules, sachets, granules, powders, suspensions, emulsions, anhydrous or hydrous topical formulations and solutions.

The pharmaceutical acceptable carriers or vehicles are well-known to those skilled in the art and are readily available to the public. It is preferred that the pharmaceutically acceptable carrier or vehicle be one which is chemically inert to the active formulation and each of its components and one which has no detrimental side effects or toxicity under the conditions of use.

In some embodiments, the pharmaceutical composition is adapted as a delivery system for transporting the therapeutic agent orally, topically, parenterally or intravenously into the circulatory system of a subject.

Formulations suitable for oral administration include liquid solutions, such as an effective amount of the nanoparticles, or composition comprising the same, dissolved in diluents, such as water or saline; capsules, sachets, tablets, lozenges, each containing a predetermined amount of the nanoparticles; powders; suspensions in an appropriate liquid; and emulsions.

Topical formulations include aqueous ophthalmic solutions or suspensions, ophthalmic ointment, ocular insert or any other formulation able to supply the nanoparticles to the external eye surface. Preferably, the topical formulation is an ophthalmic solution or suspension containing the nanoparticles for application as a liquid drop. Any of the formulations mentioned above can include a suitable solvent, preservatives and other pharmaceutically acceptable excipient commonly found in ocular formulations.

The parenteral formulations will typically contain from 0.5 to 25% by weight of the nanoparticles in solution. Said formulations can be presented in unit-dose or multi-dose sealed containers, such as ampules and vials, and can be stored in freeze-dried (lyophilized) conditions requiring only the addition of the sterile liquid carrier, for example, water for injections, immediately prior to use.

Diseases to be Treated

As mentioned above, the nanoparticles of albumin and monoclonal antibody have shown to be a very promising drug delivery system for the treatment of ocular diseases and cancer.

Therefore, another aspect of the present invention relates to a nanoparticle or composition as defined above for use in the treatment of ocular diseases.

In a particular embodiment of this aspect, the nanoparticle comprises a solid core, said solid core comprising a non-cross-linked albumin matrix and a monoclonal antibody, and wherein the monoclonal antibody is distributed throughout the albumin matrix, said solid core is not coated with any polymer. More particularly, said solid core is not coated with a non-ionic polymer.

In another particular embodiment of this aspect, the nanoparticle comprises a solid core, said solid core consisting of a non-cross-linked albumin matrix and a monoclonal antibody, and wherein the monoclonal antibody is distributed throughout the albumin matrix, said solid core is not coated with any polymer. More particularly, said solid core is not coated with a non-ionic polymer.

In another particular embodiment of this aspect, the nanoparticle consists of a solid core, said solid core comprising a non-cross-linked albumin matrix and a monoclonal antibody, and wherein the monoclonal antibody is distributed throughout the albumin matrix, said solid core is not coated with any polymer. More particularly, said solid core is not coated with a non-ionic polymer.

In another particular embodiment of this aspect, the nanoparticle consists of a solid core, said solid core consisting of a non-cross-linked albumin matrix and a monoclonal antibody, and wherein the monoclonal antibody is distributed throughout the albumin matrix, said solid core is not coated with any polymer. More particularly, said solid core is not coated with a non-ionic polymer.

In another aspect, the invention also relates to a method for the treatment of an ocular disease, said method comprises administering to a subject in need of such treatment a nanoparticle or composition comprising the nanoparticles as described above.

In yet another aspect, the invention also relates to the use of a nanoparticle or composition comprising the nanoparticles as described above for the manufacture of a medicament for the treatment of ocular diseases.

Said composition may be administered to the subject orally, topically or via intra-ocular injection. In a preferred embodiment, the composition is administered topically, such as for example by means of a route of access to ocular mucosae, or by intravitreal injection.

Thus, in a preferred embodiment, when nanoparticles are administered for the treatment of an ocular disease, said nanoparticles are administered in a topical or injectable pharmaceutical composition such as those described herein above.

In another particular embodiment, the ocular disease to be treated is selected from macular degeneration, corneal neovascularization or angiogenesis, iris neovascularization or angiogenesis, retinal neovascularization or angiogenesis, diabetic proliferative retinopathy, non-diabetic proliferative retinopathy, glaucoma, infective conjunctivitis, allergic conjunctivitis, ulcerative keratitis, non-ulcerative keratitis, episcleritis, scleritis, diabetic retinopathy, uveitis, endophthalmitis, infectious conditions and inflammatory conditions.

Another aspect of the present invention refers to a nanoparticle or composition as defined above for use in the treatment of cancer.

In a particular embodiment of this aspect, the nanoparticle comprises a solid core, said solid core comprising a non-cross-linked albumin matrix and a monoclonal antibody, and wherein the monoclonal antibody is distributed throughout the albumin matrix, said solid core being coated with a non-ionic polymer.

In another particular embodiment of this aspect, the nanoparticle comprises a solid core, said solid core consisting of a non-cross-linked albumin matrix and a monoclonal antibody, and wherein the monoclonal antibody is distributed throughout the albumin matrix, said solid core being coated with a non-ionic polymer.

In another particular embodiment of this aspect, the nanoparticle consists of a solid core, said solid core comprising a non-cross-linked albumin matrix and a monoclonal antibody, and wherein the monoclonal antibody is distributed throughout the albumin matrix, said solid core being coated with a non-ionic polymer.

In another particular embodiment of this aspect, the nanoparticle consists of a solid core, said solid core consisting of a non-cross-linked albumin matrix and a monoclonal antibody, and wherein the monoclonal antibody is distributed throughout the albumin matrix, said solid core being coated with a non-ionic polymer.

In another aspect, the invention also relates to a method for the treatment of cancer, said method comprises administering to a subject in need of such treatment a nanoparticle or composition comprising the nanoparticles as described above.

In yet another aspect, the invention also relates to the use of a nanoparticle or composition comprising the nanoparticles as described above for the manufacture of a medicament for the treatment of cancer.

In a preferred embodiment, said composition is administered parenterally to the individual, for example, by intravenous, intra-arterial, intramuscular or subcutaneous administration.

Thus, in a preferred embodiment, when nanoparticles are administered for the treatment of cancer, said nanoparticles are administered in a parenteral formulation such as those described herein above.

In another particular embodiment, the cancer to be treated includes, but is not limited to, carcinoma, lymphoma, blastoma, sarcoma and leukemia. Examples of cancer to be treated by the administration of nanoparticles include, for example, breast cancer, lung cancer, pancreatic cancer, multiple myeloma, renal cell carcinoma, prostate cancer, melanoma, colon cancer, colorectal cancer, kidney cancer, cervical cancer, ovarian cancer, liver, renal and gastric cancer, bladder cancer or squamous cell cancer.

In some embodiments, the nanoparticles used in the present invention, or the compositions containing them, may be administered with a second therapeutic compound and/or second therapy, either for the treatment of ocular diseases or of cancer.

The dosing frequency of the composition and the second compound or second therapy may be adjusted over the course of the treatment. In some embodiments, the first and second therapies are administered simultaneously, sequentially, or concurrently. When administered separately, the nanoparticle composition and the second compound can be administered at different dosing frequency or intervals.

Alternatively, the nanoparticles used in the present invention may comprise a second monoclonal antibody or therapeutic agent in order to also provide a combination therapy.

Said therapeutic agent includes, for example, other proteins such as calcitonin, insulin or cyclosporine A.

The second monoclonal antibody can be any of those mentioned herein above, such as, bevacizumab (Avastin®), ranibizumab (Lucentis®), trastuzumab (Herceptin®), cetuximab (Erbitux®) or rituximab (Mabthera®).

EXAMPLES

In the examples provided below, the following abbreviations are used:
BEVA: Bevacizumab
B-NP: Bevacizumab-loaded albumin nanoparticles
HSA: Human serum albumin
PM: physical mixture
NP-Glu: Albumin nanoparticles cross-linked with glutaraldehyde
B-NP-GLU: Bevacizumab-loaded albumin nanoparticles cross-linked with glutaraldehyde
NP-PEG35: Albumin nanoparticles coated with polyethylene glycol 35,000
B-NP-PEG35: Bevacizumab-loaded albumin nanoparticles coated with polyethylene glycol 35,000
B-NP-HPMC-P: Bevacizumab-loaded albumin nanoparticles coated with hydroxypropyl methyl cellulose phthalate
B-NP-S100: Bevacizumab-loaded albumin nanoparticles coated with Eudragit S-100

Materials

Human serum albumin or HSA (fraction V, purity 96-99%), polyethylene glycol 35,000 (PEG35), and glutaraldehyde (GLU) 25% aqueous solution were obtained from Sigma (Madrid, Spain).

Bevacizumab (Avastin®) was purchased from Roche (Spain). Hydroxypropyl methyl cellulose K100 LV (HPMC; MW 164,000) from Ashland Chemical Hispania (Spain). Avastin® is provided as a concentrate for solution for infusion in a single use vial, which contains a nominal amount of either 100 mg of bevacizumab in 4 mL or 400 mg of bevacizumab in 16 ml (concentration of 25 mg/mL). Hydroxypropyl methylcellulose phthalate (HPMC-P) was purchased from Acros Organic (Spain). Micro BCA protein assay kit was purchased from Pierce (Thermo Fisher Scientific Inc. (Illinois, USA). The Shikari Q-beva Enzyme immunoassay used for the detection of bevacizumab was purchased from Matriks Biotech (Turkey). The acetone was purchased from Prolabo, VWR International Ltd (England) and tin chloride dihidrate and absolute ethanol was purchased from Panreac Pharma (Spain). Isofluorone was from Braun, and euthanasic T-69 Intervet from Schering-Plough Animal Health. Technetium-99m pertechnetate eluate was obtained from a Drytec® $^{99}$Mo-$^{99m}$Tc generator purchased from General Electric.

For the physico-chemical studies the following devices were used: Thermo/Nicolet 360FT-IR (E.S.P.Thermo Fisher Scientific, USA), a diffractometer Bruker Axs D8 Advance (Germany), for thermo gravimetric analysis (TG) and differential scanning calorimetry a (DSC) Mettler Toledo dsc822e was used with the Mettler Toledo TSO 801RO Sample Robot and Julabo FT900 cooler, and for elemental analysis an Elemental Analyzer from LECO CHN-900 (Michigan USA).

For radiolabelling and biodistribution studies the following devices were used: Symbia SPECT/CT, Siemens Medical Systems, Germany, Activimeter AtomLab 500, Biodex, USA, Gamma counter, LKB Pharmacia.

Physico-Chemical Characterization of Nanoparticles (Size, Zeta Potential and Morphology)

The particle size and zeta potential of nanoparticles were determined in a Zeta Plus apparatus (Brookhaven Inst. Corp., USA). The diameter of the nanoparticles was determined after dispersion in ultrapure water (1/10) and measured at 25° C. by dynamic light scattering angle of 90° C. The zeta potential was determined as follows: 200 µL of the samples was diluted in 2 mL of a 1 mM KCl solution adjusted to pH 7.4.

The morphological characteristics of the nanoparticles were studied by scanning electron microscopy (SEM) in a Zeiss DSM940 digital scanning electron microscope (Oberkochen, Germany). For this purpose, samples were dispersed in water and centrifuged at 27,000×g for 20 min at 4° C. in order to eliminate the cryoprotector. Then, the pellets were mounted on glass plates adhered with a double-sided adhesive tape onto metal stubs and dried. They were coated with a palladium-platinum layer of 4 nm using a Cressington sputter-coater 208HR with a rotary-planetary-tilt stage, equipped with an MTM-20 thickness controller. SEM was performed using a LEO 1530 apparatus (LEO Electron Microscopy Inc, Thornwood, N.Y.) operating between 1 and 3 kV with a filament current of about 0.5 mA.

Yield

The amount of HSA transformed into nanoparticles (yield) was determined through the quantification of the HSA forming the nanoparticles by a Micro BCA. Briefly, 10 mg of the nanoparticles were weighed and dispersed in 10 mL of ultrapure water and centrifuged at 15,000 rpm for 15 min at 4° C. (Rotor 3336, Biofuge Heraeus, Hanau, Germany). Then, the pellet was broken with 1 mL of NaOH 0.02 N and 200 µL of this solution was transferred to a 96-well microplate and proceeded to follow a specific micro-BCA protein assay kit in a spectrophotometer at 562 nm.

The selectivity of the kit was determined by using controls containing the other excipients and drugs (glutaraldehyde, PEG 35,000, HPMC or bevacizumab) in order to detect any possible interference in albumin determinations. Data analysis was performed using the following equation:

$$\text{Yield (\%)} = (W\text{lyop}/W\text{initial}) \times 100 \quad [\text{eq. 1}]$$

where Wlyop was the HSA that was transformed into nanoparticles and Winitial was the amount of HSA used to prepare the nanoparticles.

Quantification of Drug Payload in Nanoparticles

The amount of the antibody loaded in albumin nanoparticles was estimated by enzyme immunoassay (Shikari Q-BEVA). For this purpose, 10 mg of the nanoparticles were weighed and dispersed in 1 mL water. The suspension was centrifuged for 10 min at 10,000 rpm (Rotor 3336, Biofuge Heraeus, Hanau, Germany). The supernatant was removed. Then the nanoparticles were broken with 1 ml of NaOH 0.02N. 200 µL of the resulting solution was transferred to a 96-well microplate coated with human vascular endothelial growth factor (VEGF) and followed a specific ELISA for bevacizumab (Q-Beva test procedure, Shikari Q-Beva, Matriks Biotek).

Each sample was assayed by triplicate and the calculations were performed using standard curves in the range between 0.1 and 100 µg/mL (r2>0.993). The detection and quantification limits were 0.1 µg/mL and 100 µg/mL respectively (r2>0.993). The bevacizumab loading (DL) and its encapsulation efficiency (EE) were calculated according to the following equations:

$$DL = [W\text{encap}/W\text{np}] \quad [\text{eq. 2}]$$

$$EE = [W\text{encap}/W\text{total}] \times 100 \quad [\text{eq. 3}]$$

where Wencap was the amount of bevacizumab encapsulated, Wtotal was the total amount of the drug used and Wnp was the nanoparticles weight.

FT-IR Determinations

The molecular structure of HSA nanoparticles was investigated by means of FTIR spectroscopy. The infrared spectra of the samples dispersed at 1% of sample in KBr discs were recorded in a NICOLET FTIR spectrometer (Thermo/Nicolet 360FT-IR E.S.P.Thermo Fisher Scientific, USA). The samples were scanned from 4000 to 400 cm−1. The recording conditions were as follows: resolution of 8.0 and sample scan of 40. Data were analyzed using the OMNIC software (Thermo Fisher Scientific, USA).

X-Ray Studies

X-ray studies were performed in order to study the distribution of the crystallographic planes and crystallinity variability of the polymer matrix in the different samples of nanoparticles. For this purpose, the samples were placed in powder form on a metal plate in a diffractometer (Bruker Axs D8 Advance, Germany)—and measures over 360 were performed at room temperature. The diffractograms were analyzed using the program Diffrac. Suite.

Thermal Analysis

The response of the different nanoparticles to temperature changes was studied by thermal analysis (thermogravimetric analysis TGA coupled to differential thermal analysis DTA). The variations of thermal behavior of the functional groups of the HSA, when this reacts to form the nanoparticles, were analysed. The thermal studies were carried out with a simultaneous TGA/sDTA 851e Mettler Toledo thermal analyzer. The thermograms were obtained by heating about 5-10 mg of the sample in a pierced aluminium crucible at a scan rate of 10° C./min from 25 to 250° C. The thermal analyses were performed under static air atmosphere and $N_2$ (20 mL min$^{-1}$) as purge gas. The measurements were made in triplicate.

Elemental Analysis

Elemental analysis (C, H, O and N) of the nanoparticles was performed in order to confirm the association of the different stabilizing agents in the HSA nanoparticles Elemental Analyzer from LECO CHN-900, Michigan USA). Briefly, 1 mg of each sample was tested in triplicate and results were expressed as a percentage (% w/w) SD±0.4. This technique shows changes in the composition of oxygen, hydrogen or nitrogen of albumin (HSA) when associated with other components (glutaraldehyde, PEG35, HPMC-P or bevacizumab).

In Vitro Release Study

In vitro release studies of bevacizumab-loaded albumin nanoparticles were carried out in PBS (pH 7.4). Eppendorf tubes containing 10 mg of each nanoparticle formulation were dispersed in a total volume of 1 mL PBS, distributed in eppendorf tubes, and placed in a shaking bath at 37° C. with a constant agitation of 60 strokes/min (Unitronic 320 OR, Selecta, Madrid, Spain). At different time intervals, eppendorf tubes were taken and centrifuged for 10 min at 10,000 rpm (Rotor 3336, Biofuge Heraeus, Hanau, Germany). The supernatants were analysed for bevacizumab content with the specific ELISA test (Shikari Q-Beva, Matriks Biotek). Release profiles were expressed in terms of cumulative release in percentage, and plotted versus time.

Furthermore, on the basis of the release profiles, the kinetics were examined by the Korsmeyer-Peppas equation exponential model (eq. 4):

$$Q = Kt^n \qquad [\text{eq. 4}]$$

where Q is the percentage of drug released at time t and K is a constant incorporating the structural and geometric characteristics of the device under investigation, and "n" is the diffusional exponent, which is typically utilized as indicator of the mechanism of drug transport from the dosage form.

A value of n≤0.43 indicates that drug release is controlled by Fickian diffusion, whereas a value of n≥0.85 suggests that drug release is dominated by an erosion mechanism. For values 0.43<n<0.85, the release is described as anomalous, implying that a combination of diffusion and erosion contributes to the control of drug release [Gao Y., et al., In Vitro Release Kinetics of Antituberculosis Drugs from Nanoparticles Assessed Using a Modified Dissolution Apparatus. Biomed Research International 2013].

Example 1. Preparation of Bevacizumab-Loaded Human Serum Albumin Nanoparticles. Influence of the Bevacizumab/HSA Ratio on the Physico-Chemical Properties of the Resulting Nanoparticles Bevacizumab-loaded nanoparticles were prepared by a procedure in which nanoparticles were obtained by precipitation of the proteins in an aqueous environment before purification and drying.

For this purpose, 100 mg HSA and a variable amount of bevacizumab (BEVA) (1-20 mg) were dissolved in 5-10 mL of water for injection and, then, the solution was titrated to pH 4.1-4.4 with HCL 1 M. The mixture was incubated at room temperature for 10 minutes. Nanoparticles were obtained by the continuous addition of 16 mL of ethanol used as desolvating agent under continuous stirring (500 rpm) at room temperature. The resulting nanoparticles were purified by two different procedures: ultracentrifugation and ultrafiltration. In the former, nanoparticles were purified twice by centrifugation at 21,000×g for 20 min at 4° C. (Sigma 3K30, Osterodeam Harz, Germany) and redispersion of the pellet in the original volume in water. In the latter, nanoparticles were purified by ultrafiltration through a polysulfone membrane cartridge of 50 kDa pore size (Medica SPA, Italy). Finally, nanoparticles were freeze-dried in a Genesis 12EL apparatus (Virtis, NewYork, USA) after redispersion or addition of an aqueous solution of sucrose 5%. These formulations are bevacizumab-loaded human serum albumin nanoparticles, without any further stabilization, hereinafter B-NP formulations.

For the encapsulation of the monoclonal antibody in the nanoparticles, two key parameters were identified: the bevacizumab/albumin ratio and the time of incubation between both compound prior the formation of nanoparticles. Table 1 summarizes the main physico-chemical properties of the resulting nanoparticles by varying the monoclonal antibody/protein ratio. When the bevacizumab/albumin ratio was low (e.g. 0.01), nanoparticles were not stable with time. For ratios higher than 0.01, the resulting nanoparticles were stable with a mean size close to 300 nm and a negative surface charge of about −15 mV.

Figure 1:
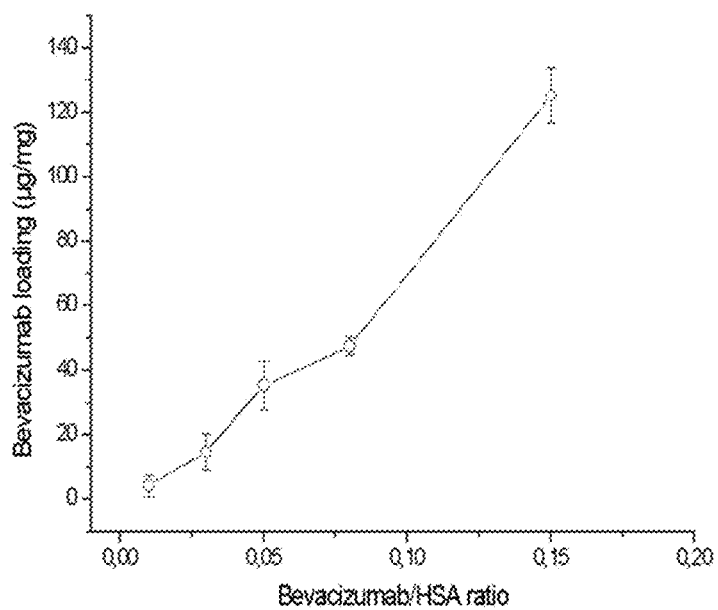
FIG. 1. Influence of the bevacizumab/albumin ratio on the payload of the resulting nanoparticles. Nanoparticles were prepared after the incubation for 10 min of the monoclonal antibody and the protein. Data expressed as mean±SD (n=3).

Similarly, the yield of the process was calculated to be around 80%. FIG. 1 shows the effect of the bevacizumab/albumin ratio on the monoclonal antibody loading.

In accordance with these results, the amount of bevacizumab loaded in nanoparticles increased by increasing the BEVA/HSA ratio. All of these experiments were carried out after 10 min of incubation between the monoclonal antibody and the protein. Interestingly, no significant differences on the physicochemical properties of nanoparticles were observed by increasing this parameter.

TABLE 1

Influence of the bevacizumab/albumin ratio on the physico-chemical properties of the resulting nanoparticles. Time of incubation between bevacizumab and albumin: 10 min. Data expressed as mean ± SD (n = 3).

| BEVA/HSA ratio | Mean size (nm) | PDI | Zeta potential (mV) | Yield (%) |
|---|---|---|---|---|
| 0.01 | 240 ± 3 | 0.27 ± 0.01 | −18.9 ± 0.9 | 75 |
| 0.03 | 326 ± 7 | 0.21 ± 0.03 | 14.1 ± 0.3 | 78 |
| 0.05 | 353 ± 6 | 0.26 ± 0.01 | −11.7 ± 0.2 | 78 |
| 0.08 | 304 ± 4 | 0.16 ± 0.03 | −15.5 ± 0.3 | 80 |
| 0.15 | 306 ± 4 | 0.22 ± 0.01 | −16.1 ± 0.3 | 85 |

Example 2. Influence of the Cross-Linkage of Bevacizumab-Loaded Nanoparticles with Glutaraldehyde on their Physico-Chemical Properties Due to the fact that human serum albumin nanoparticles in the absence of bevacizumab were not stable and disappeared just after formation, control bevacizumab-loaded nanoparticles were obtained after cross-linkage with 12.5 µg glutaraldehyde in ethanol (300 µl), hereinafter B-NP-GLU formulations. For this purpose, the just formed bevacizumab-loaded nanoparticles were incubated for 5 min with glutaraldehyde before purification and freeze-drying.

Table 2 summarizes the main physico-chemical properties of "naked" HSA nanoparticles (without any further stabilization procedure) and the control ones obtained after cross-linkage with glutaraldehyde. The encapsulation of bevacizumab in albumin nanoparticles produced stable nanoparticles with high antibody contents. Interestingly, the encapsulation efficiency calculated as the active monoclonal antibody loaded in nanoparticles was close to 90% with a bevacizumab loading of about 13%. When bevacizumab-loaded nanoparticles were cross-linked with glutaraldehyde, the resulting nanoparticles were slightly smaller than those produced without the chemical cross-linking agent. However, the treatment of nanoparticles with glutaraldehyde inactivated the monoclonal antibody and very low levels of the antibody were quantified by the ELISA analysis.

TABLE 2

Physico-chemical characteristics of non-treated and glutaraldehyde cross-linked albumin nanoparticles. Nanoparticles were prepared at a bevacizumab/albumin ratio of 0.15 and 10 min of incubation prior the formation of nanoparticles.

|  | Size (nm) | PDI | Zeta potential (mV) | Yield (%) | BEVA loading (μg/mg NP) | EE (%) |
|---|---|---|---|---|---|---|
| NP | NA | NA | NA | NA | — | — |
| B-NP | 310 ± 3 | 0.14 ± 0.02 | −14 ± 1 | 85 ± 3 | 132 ± 5 | 89 ± 0 |
| NP-GLU | 163 ± 2 | 0.17 ± 0.01 | −36 ± 0 | 66 ± 5 | — | — |
| B-NP-GLU | 270 ± 3 | 0.11 ± 0.03 | −39 ± 1 | 68 ± 2 | 0.1 ± 0.3 | 0.1 ± 1.3 |

Data expressed as mean +/− SD (n = 3).
PDI: polydispersity index; BEVA: bevacizumab; EE: encapsulation efficiency; NP: nanoparticles; GLU: glutaraldehyde.

Example 3: Characterization of Bevacizumab-Loaded Nanoparticles

TEM

Figure 2:
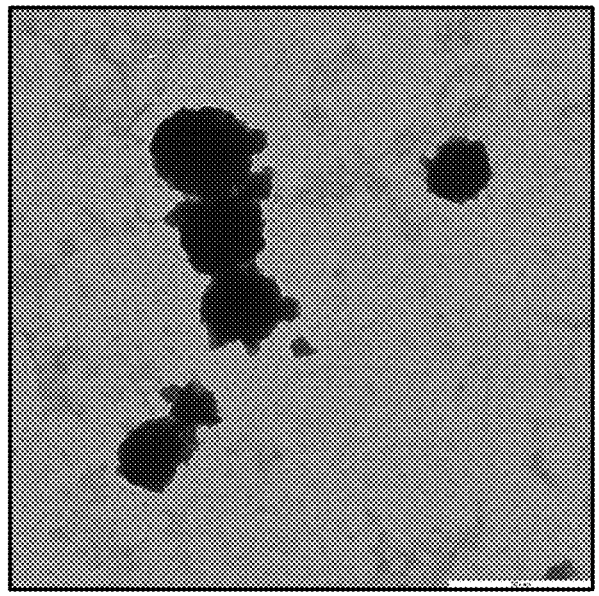
FIG. 2. TEM photograph of bevacizumab-loaded albumin nanoparticles (B-NP).

FIG. 2 shows the morphology of the bevacizumab-loaded nanoparticles (B-NP), which has a spherical shape and an irregular surface.

FT-IR Determinations

Figure 3:
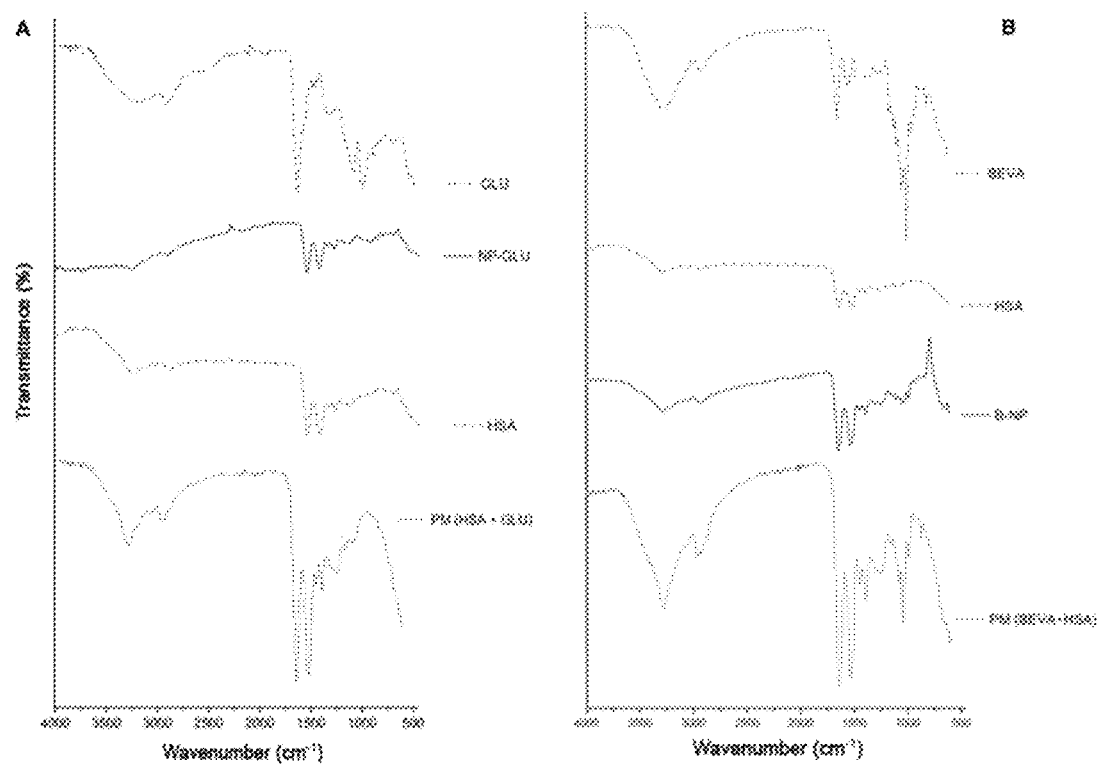
FIG. 3. A) FT-IR spectrum of human serum albumin (HSA), glutaraldehyde (GLU), physical mixture between HSA and glutaraldehyde (HSA-GLU), and nanoparticles cross-linked with glutaraldehyde (NP-GLU). B) FT-IR spectrum of human serum albumin (HSA), bevacizumab (BEVA), physical mixture between HSA and bevacizumab (HSA-BEVA), and bevacizumab-loaded nanoparticles (B-NP).

IR permits to evaluate the apparition of conformational changes in the secondary structure of the protein. FIG. 3 shows the FT-IR spectra of bevacizumab-loaded nanoparticles compared to those of the monoclonal antibody alone and the protein, and the physical mixture thereof.

Infrared spectra of proteins exhibit a number of amide bands, which represent different vibrations of peptide moieties. Such signals, amide I band ranging from 1600 to 1700 $cm_{-1}$ (mainly C=O stretch) and amide II band at 1550 $cm^{-1}$ (C—N stretch coupled with N—H bending mode) have been used as evidence of the presence of this chemical bound and they are directly related to secondary structure of the protein. However, the amide I band is more sensitive to the change of protein secondary structure than amide II. In this way, changes in the frequencies and intensities of these signals are evidences of interaction with the protein.

In this case, and due to the fact, that nanoparticles are formed by two different proteins (albumin and bevacizumab) a small variation of the frequency of the signal corresponding to the amide I peak was observed (1642 for HSA and 1645 $cm^{-1}$ for B-NP).

As a control, nanoparticles cross-linked with glutaraldehyde were also studied. In this case, also a slight displacement of the frequencies of the amide I (1642 to 1645 $cm^{-1}$) was found as a result of the interaction between the glutaraldehyde and the albumin.

X-Ray Studies

Figure 4:
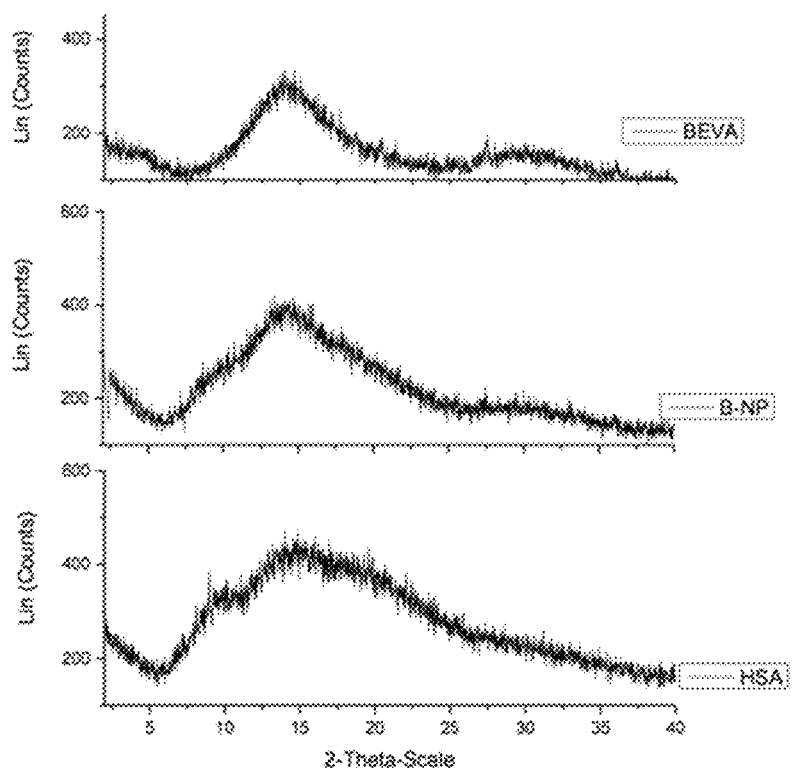
FIG. 4. X-ray spectra of bevacizumab (BEVA), bevacizumab-loaded nanoparticles (B-NP) and human serum albumin (HSA).

FIG. 4 shows the X-ray sprectra of human serum albumin, bevacizumab and bevacizumab-loaded nanoparticles. In all cases, these spectra show an amorphous structure.

Thermal Analysis

Figure 5:
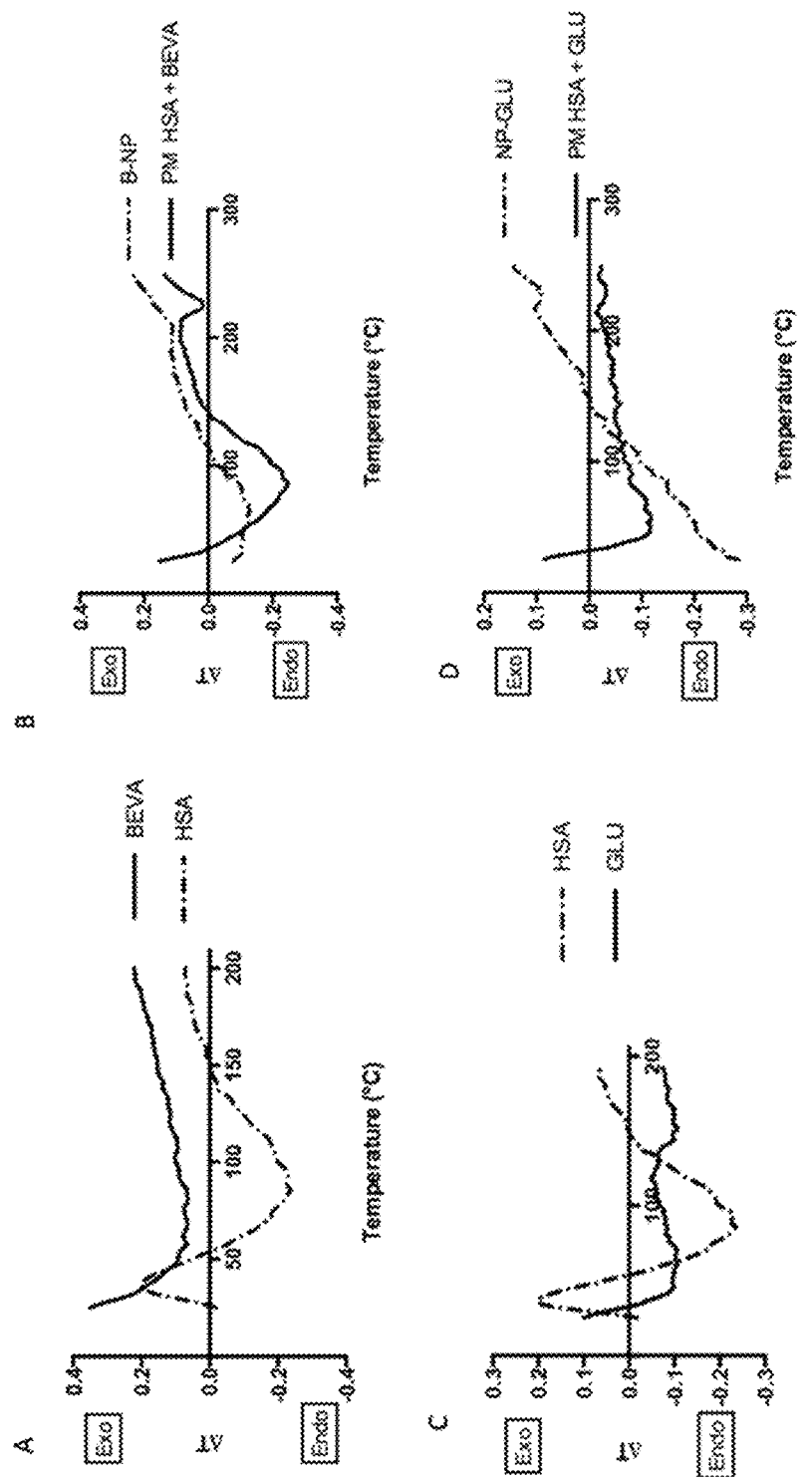
FIG. 5. DTA thermograms of: A) native human serum albumin (HSA) and bevacizumab (BEVA); B) physical mixture (PM) between human serum albumin (HSA) and bevacizumab (BEVA) and the bevacizumab loaded-albumin nanoparticles (B-NP); C) native human serum albumin (HSA) and glutaraldehyde (GLU); D) physical mixture (PM) between human serum albumin (HSA) and glutaraldehyde (GLU) and the albumin nanoparticles cross-linked with glutaraldehyde (NP-GLU).

Thermal analyses were performed to determine the reaction between functional groups of the HSA and bevacizumab. FIG. 5 shows the thermograms of the native albumin (HSA) and bevacizumab (BEVA) (A), the bevacizumab nanoparticles (B-NP) and the physical mixture (P.M.) of albumin and bevacizumab (B), the native albumin (HSA) and glutaraldehyde (GLU) (C), the glutaraldehyde cross-linked nanoparticles (NP-GLU) and the physical mixture (P.M.) of albumin and glutaraldehyde (D).

The thermograms show that native albumin presents an exothermic effect around 30° C., that corresponds to a reversible transition and a second thermal effect due to an endothermic glassy transition at about.

The absence of the exothermic signal corresponding to the albumin in the NPs could be attributed to a combination of the albumin with both protein (BEVA) and cross-linking agent (glutaraldehyde). Thus, bevacizumab and albumin would form a complex.

Elemental Analysis

Table 3 shows the elemental analysis of human serum albumin, bevacizumab, albumin nanoparticles cross-linked with glutaraldehyde and bevacizumab-loaded albumin nanoparticles. Bevacizumab displays a significant lower content of carbon and nitrogen than human serum albumin. On the contrary, the oxygen content in the monoclonal antibody is about 2-times higher than in albumin. In a similar way, bevacizumab-loaded nanoparticles (B-NP) presented a lower percentage of nitrogen and a higher content in oxygen than the native albumin.

TABLE 3

Elemental analysis of human serum albumin (HSA), bevacizumab (BEVA), albumin nanoparticles cross-linked with glutaraldehyde (NP-GLU) and bevacizumab-loaded nanoparticles (B-NP).

|  | % C | % H | % N | % O |
|---|---|---|---|---|
| HSA | 48.34 | 6.96 | 17.80 | 26.91 |
| BEVA | 36.70 | 6.64 | 4.25 | 52.41 |
| NP-GLU | 48.09 | 6.87 | 15.19 | 29.85 |
| B-NP | 48.77 | 6.86 | 14.90 | 29.48 |

Example 4: Stability of Bevacizumab-Loaded Nanoparticles

The stability of the nanoparticles was evaluated in ultrapure water. The samples were dispersed in purified water and stored at room temperature for 3 days. At different time intervals the stability was assessed by measuring the size, polydispersity index and zeta potential of the nanoparticles.

Figure 6:
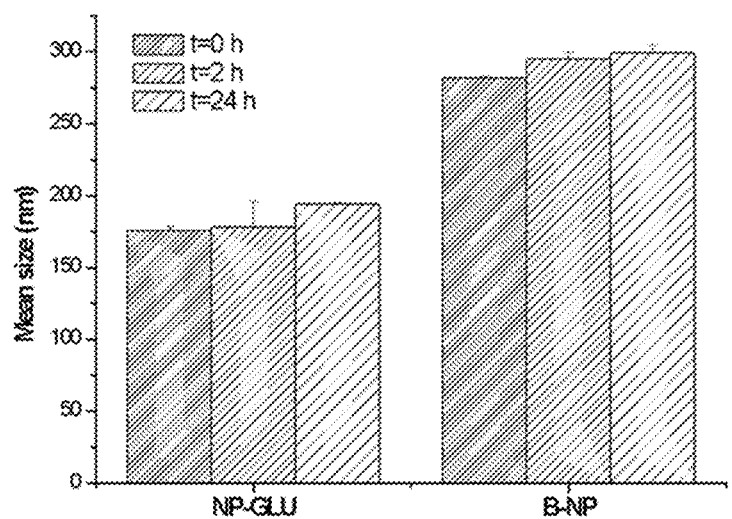
FIG. 6. Evolution of the mean size of empty nanoparticles cross-linked with glutaraldehyde (NP-GLU) and bevacizumab-loaded nanoparticles (B-NP) after their dispersion in an aqueous solution at pH 7.4. Data expressed as mean+SD (n=3).

After dispersion in water (pH adjusted to 7.4), bevacizumab-loaded nanoparticles were stable for at least 24 hours (FIG. 6). Their behavior was similar to that observed for empty nanoparticles cross-linked with glutaraldehyde (FIG. 6). In a similar way, the polydispersity index (PDI) of B-NP was not affected during the experiment. Thus, at t=0, the PDI was 0.19±0.01, and 24 hours later, this parameter was calculated to be 0.16±0.03 (data not shown).

Example 5: In Vitro Release of Bevacizumab from Nanoparticles

Figure 7:
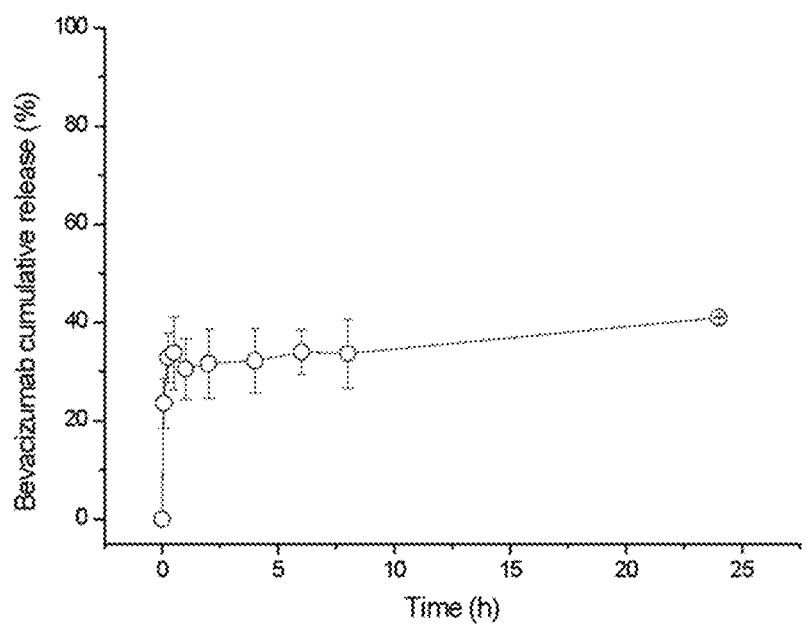
FIG. 7. Bevacizumab release profile from human serum albumin nanoparticles after incubation in PBS (pH 7.4). Data expressed as mean+SD (n=3).

FIG. 7 shows the in vitro release profile of bevacizumab from albumin nanoparticles in PBS. This profile was characterised by an initial burst effect of about 23% of the loaded antibody during the first 5 min followed a slow controlled release during the following 24 hours. At the end of the experiment, around 40% of the loaded bevacizumab was released. The burst release could be related to antibody adsorbed on the surface of the nanoparticles.

Example 6. Preparation and Characterization of Bevacizumab-Loaded Coated Albumin Nanoparticles The encapsulation of bevacizumab in human serum albumin nanoparticles decorated with different compounds was prepared by a procedure involving 4 steps. Particularly, non-ionic HPMC-P and PEG35 were selected to explore their capabilities to decorate bevacizumab-loaded nanoparticles. The ionic coating Eudragit S-100 was also used.

The first step was dedicated to the production of nanoparticles in an aqueous environment. Then the surface of nanoparticles was decorated by simple incubation in an aqueous environment. The third step was used to purify the resulting nanoparticles that, finally, were dried.

First step. 100 mg HSA and a variable amount of bevacizumab (1-20 mg) were dissolved in 5-10 mL of water for injection and, then, the solution was titrated to pH 4.1-4.4 with HCl 1 M. The mixture was incubated at room temperature for 10 minutes. Nanoparticles were obtained by the continuous addition of 16 mL of ethanol used as desolvating agent under continuous stirring (500 rpm) at room temperature.

Second step. For the coating of the just formed bevacizumab-loaded nanoparticles, one of the following compounds was added: PEG 35,000, hydroxymethylpropyl cellulose phthalate or Eudragit S-100.

As control, bevacizumab-loaded nanoparticles were stabilized by cross-linkage with 12.5 µg glutaraldehyde in ethanol (300 µL) for 5 minutes as described above.

Third step. The resulting nanoparticles were purified. Two different procedures were used: ultracentrifugation and ultrafiltration. In the former, nanoparticles were purified twice by centrifugation at 21,000×g for 20 min at 4° C. (Sigma 3K30, Osterodeam Harz, Germany) and redispersion of the pellet in the original volume in water. In the latter, nanoparticles were purified by ultrafiltration through a polysulfone membrane cartridge of 50 kDa pore size (Medica SPA, Italy).

Fourth step. Finally, nanoparticles were freeze-dried in a Genesis 12EL apparatus (Virtis, NewYork, USA). When ultracentrifugation was used as purification method, the pellet from the last centrifugation was dispersed in an aqueous solution of sucrose 5%. When ultrafiltration was used, the pellet was also redispersed in an aqueous solution of sucrose 5% before lyophilisation.

Table 4 summarises the main physico-chemical properties of these nanoparticles. Overall, the amount of loaded bevacizumab was always similar and close to 14%. Nevertheless the incubation of bevacizumab-loaded nanoparticles with the different excipients for coating purposes, yielded nanoparticles with modified physico-chemical properties. Thus, PEG35-coated nanoparticles encapsulating bevacizumab (B-NP-PEG35) displayed similar mean sizes and negative zeta potentials as naked bevacizumab-loaded nanoparticles (B-NP). On the contrary, when B-NP were incubated with HPMC-P, the mean size of the resulting nanoparticles significantly increased, as compared with B-NP. When the incubation was carried out with ionic Eudragit® S-100, the resulting nanoparticles displayed a reduced size and an increased negative zeta potential as compared with B-NP. By SEM, albumin nanoparticles displayed a spherical shape and smooth surface.

TABLE 4

Physico-chemical characteristics of bevacizumab encapsulated into coated albumin nanoparticles.

| | CA/protein ratio; Time incubation | Size (nm) | PDI | Zeta potential (mV) | Yield (%) | BEVA loading (tig/mg NP) |
|---|---|---|---|---|---|---|
| B-NP-GLU | — | 180 ± 3 | 0.11 ± 0.01 | −36 ± 1 | 75 ± 2 | 0.1 ± 1 |
| B-NP | — | 310 ± 3 | 0.14 ± 0.02 | −14 ± 1 | 85 ± 3 | 132 ± 5 |
| B-NP-HPMC-P | 0.1; 10 min | 369 ± 1 | 0.15 ± 0.01 | −13 ± 1 | 76 ± 4 | 142 ± 4 |
| B-NP-PEG35 | 0.5; 35 min | 301 ± 2 | 0.13 ± 0.03 | −17 ± 1 | 63 ± 7 | 145 ± 6 |
| B-NP-S100 | 0.25; 10 min | 252 ± 4 | 0.07 ± 0.01 | −27 ± 1 | 86 ± 3 | 148 ± 5 |

Data expressed as mean ± SD (n = 3).
PDI: poly dispersity index.
Coating agents: S-100 (ionic Eudragit ® S100), HPMC-P (hydroxypropylmetyl cellulose phthalate), PEG35 (polyethylene glycol 35,0000).
CA/protein ratio: coating agent/albumin ratio.
B-NP-GLU: bevacizumab-loaded albumin nanoparticles cross- linked with glutaraldehyde.
B-NP: bevacizumab-loaded into "naked" albumin nanoparticles.

Figure 8:
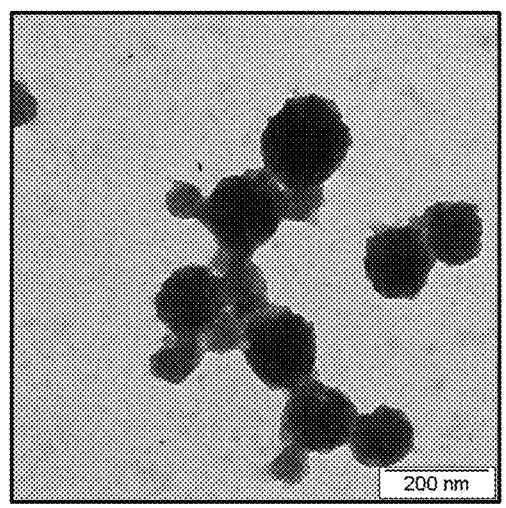
FIG. 8. TEM microphotograph of bevacizumab-loaded albumin nanoparticles pegylated with PEG35 (B-NP-PEG35).

The morphological study (FIG. 8) of the bevacizumab-loaded nanoparticles coated with PEG35 (B-NP-PEG35) shows that they are spherical with an irregular surface and a homogeneous dispersion.

Example 7: In Vitro Release of Bevacizumab from Coated Nanoparticles

Figure 9:
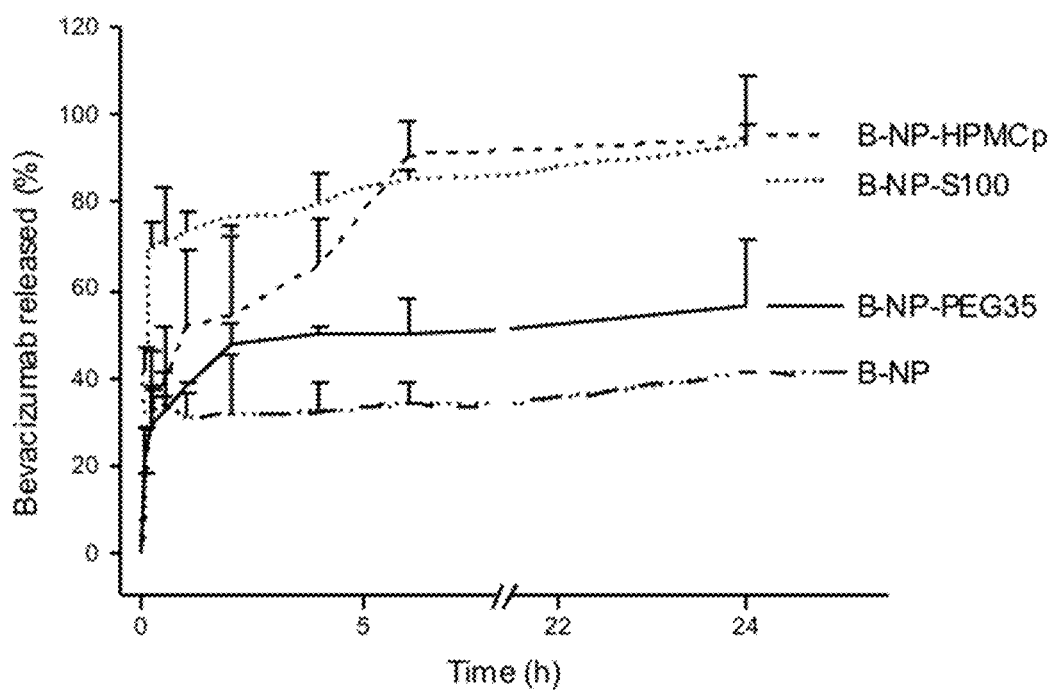
FIG. 9. Bevacizumab release profile from albumin nanoparticles after incubation in PBS (pH 7.4) (······) bevacizumab-loaded NPs (B-NP); (—) bevacizumab-loaded NPs coated with PEG35 (B-NP-PEG35); (···) bevacizumab-loaded NPs coated with Eudragit® S-100 (B-NP-S-100); (---) bevacizumab-loaded NPs coated with HPMC-P (B-NP-HPMC-P). Data expressed as mean±SD (n=3).

FIG. 9 shows the in vitro release profile of bevacizumab from albumin nanoparticles coated with two non-ionic polymers (PEG35 and HPMC-P) and with the ionic Eudragit® S100 in PBS at pH 7.4. For PEG35-coated nanoparticles (B-NP-PEG35), the profile was similar to that observed for naked nanoparticles (B-NP) with the difference that, at the end of the experiment, the amount of bevacizumab released was higher than for B-NP. In any case, these pegylated nanoparticles offered a by phasic release pattern characterised by an initial burst effect in the first 5 minutes of about 22% followed by a more sustained and slow release rate during at least 24 h. The burst release was nearly 22% and may relate to antibody adsorbed on the surface of the nanoparticles. The biphasic section, ignoring the first 5 minutes of burst release, was adjusted using the Korsmeyer-Peppas equation to a diffusion profile (n=0.54; $R^2$=0.994). During the diffusion stage the release of bevacizumab was up to 48% to reach a plateau after the first two hours.

For nanoparticles coated with HPMC-P (B-NP-HPMC-P), again, the amount of bevacizumab released during the first 60 minutes was of about 40%. Then, a continuous release rate of the remained antibody was observed. However, in this case, the release rate of bevacizumab was more rapid than for B-NP or B-NP-PEG35. Thus, after 8 h of incubation close to the 100% of the bevacizumab content was released from nanoparticles coated with HPMC-P.

Contrary to the nanoparticles coated with non-ionic polymers, the nanoparticles coated with the ionic Eudragit® S-100 (B-NP-S-100) showed an immediate release profile.

Example 8. Integrity of Bevacizumab after its Encapsulation in Albumin Nanoparticles In order to corroborate the results obtained with the ELISA kit used to quantify the amount of bevacizumab loaded in albumin nanoparticles, the integrity of the antibody (bevacizumab) encapsulated into the different nanoparticles was analyzed by microfluidic-based automated electrophoresis using an Experion™ Automated Electrophoresis System (Bio Rad, US). The samples were evaluated in non-reducing conditions and in reducing conditions, using 2-mercaptoethanol. The data obtained was processed using the software Experion System.

Nanoparticles were weighed and broken with 1 mL NaOH 0.005 N. The concentration of the different solutions was around 400 ng protein/L (linear dynamic range of the test is 5-2,000 ng/μL). Samples of free protein (albumin and bevacizumab) were used as controls. All of these samples were evaluated as obtained or after treatment with 3-mercaptoethanol and heat. Then, the samples were treated following the protocol of the Experion System Pro260 Analysis Kit (Bio-Rad Lab., USA). Once the samples and controls were loaded into the chip, they were analysed by the Experion™ Automated Electrophoresis System (Bio Rad, US).

The results were obtained as densitometric bands in a virtual gel. Each band corresponded to a different sample. The Experion software identifies the different size peaks and expressed them in kilodaltons ("kDa") in the system control band.

Figure 10:
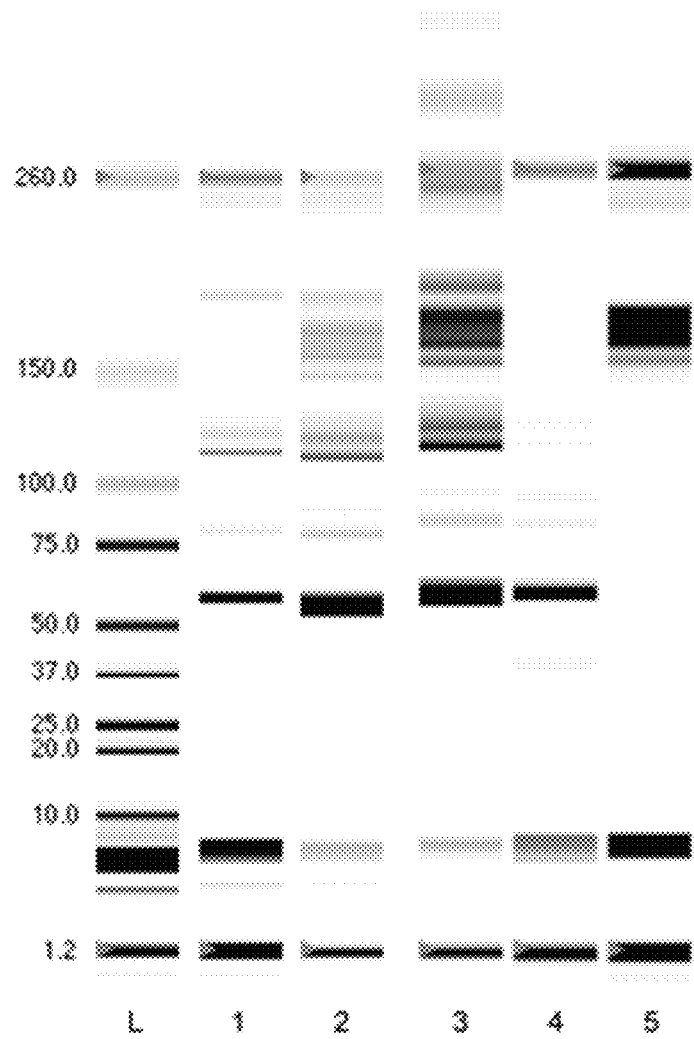
FIG. 10. Microfluidic-based automated electrophoresis of nanoparticles (L: Ladder; 1: empty nanoparticles coated with PEG35 (NP-PEG35); 2: bevacizumab-loaded albumin nanoparticles (B-NP); 3: bevacizumab-loaded albumin nanoparticles coated with PEG35 (B-NP-PEG35); 4: human serum albumin (HSA); 5: Bevacizumab).

The results of the studies are shown in FIG. 10. In lane 5, bevacizumab appears as a strong band around 150 kDa. A similar band was observed in lane 2 (B-NP) and 3 (B-NP-PEG35). Similarly, the bands corresponding to the albumin (Lane 4) also appears clearly in Lanes 1-3.

Example 9. Biodistribution Study of Nanoparticles Ocularly Administered in Wistar Rats NP Radiolabelling and Biodistribution Study in Wistar Rats for In Vivo SPECT-CT Imaging The radiolabeling of the nanoparticles was carried out with $^{99m}$Tc by reduction of $^{99m}$Tc-pertechnetate with tin chloride following a method described elsewhere. Briefly, 20 μl of a solution of tin chloride dihidrate in water for injection and a final tin concentration of 0.02 mg/ml was added to 9 mg of the lyophilized nanoparticles, followed by addition of 60 μL of $^{99m}$TcO$_4$— eluate to the pre-reduced tin. Four μL of the radiolabelled suspension of nanoparticles (5 MBq) where mixed with 0.6 mg of unlabelled nanoparticle formulation, and such mixture carefully administered on the right eye of isofluorane-anesthetised Wistar rats.

Ophthalmic Administration to Wistar Rats for In Vivo SPECT-CT Imaging

Animals were kept anesthetised for one hour to avoid active removal of the suspension from the eye, then awakened and SPECT-CT images obtained at six different time points between 5 and 17 h 30 min after administration of nanoparticles.

For imaging studies animals where anesthetised just before each study with isofluorane and placed in prone position in a Symbia T2 Truepoint SPECT-CT system (Siemens). Images where acquired using a 128×128 matrix, 7 images/s; CT was set to 110 mAs and 130 Kv, 130 images 3 mm thick. Image fusion was done using Syngo MI Applications TrueD software. Images were processed and quantified using the built-in software system. Quantitative values were obtained by automatic drawing an isocontour in the three planes over the selected areas to get Volumes of Interest (VOIs), from which the mean values of the counts were taken.

Figure 11:
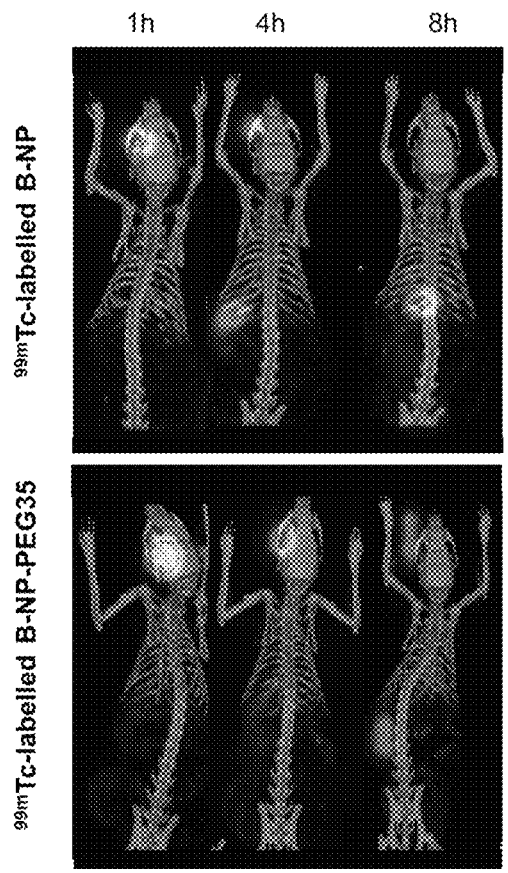
FIG. 11. In vivo SPECT-CT images of $^{99m}$Tc-labelled B-NP (upper row) compared with $^{99m}$Tc-labelled B-NP-PEG35 (bottom row) after ocular administration to Wistar rats. Images in each row correspond to the same animal studied at the time points indicated in the figure. The activity disappears between 4 h to 8 h after ocular administration while in B-NP-PEG35 remains in the eye for at least 8 h.
Figure 12:
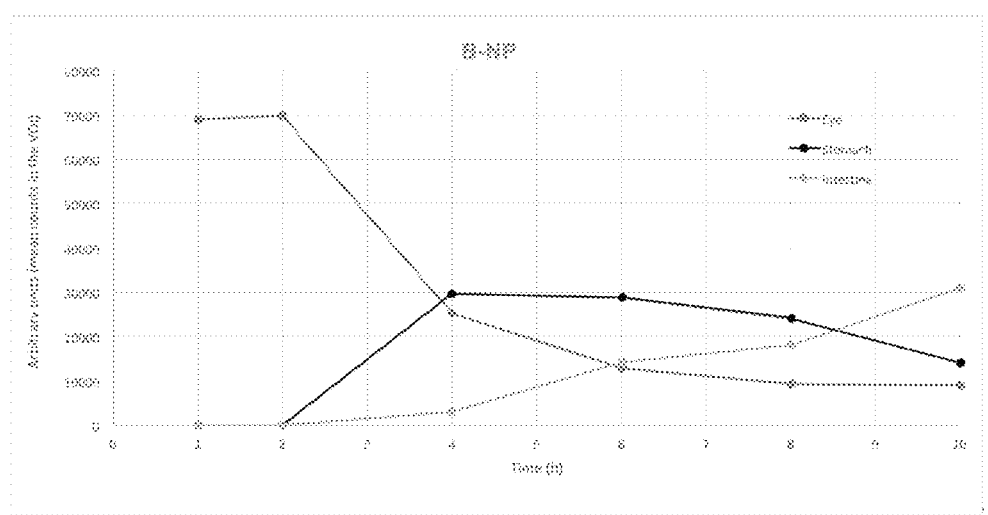
FIG. 12. Time-activity curves for the evolution of the amount of radioactivity in different regions after ocular administration of $^{99m}$Tc-B-NP nanoparticles. Volumes of interest (VOIs) were drawn over the areas denoted in the graphs and mean value counts obtained from each VOI, data corrected for decay and plotted.

FIGS. 11 and 12 show the biodistribution of B-NP and B-NP-PEG35, after ocular administration as eye drops. Radioactivity associated with nanoparticles remains in the eye for at least 4 h in the case of B-NP and for 8 h in the case of B-NP-PEG35, albeit it slowly disappears from the administration point and goes into the gastrointestinal tract. The transit of radiolabelled nanoparticles through the pharynx of the animal can be seen in the most upper left image in FIG. 11. Intensity of SPECT images in FIG. 11 has been rescaled to the highest intensity point in each individual image to better be able to appreciate the position of radioactivity in the body of the animal.

Semiquantitative decay-corrected time-course evolution of radioactivity is plotted in FIG. 12 for B-NP. The results with B-NP-PEG35 were very similar, however said nanoparticles take longer to excrete as they remain more time into the eye.

Example 10. Biodistribution of Nanoparticles after Intravenous Administration to Male Wistar Rats For in vivo biodistribution imaging experiments in Wistar rats $^{99m}$Tc labelled bevacizumab-loaded HSA nanoparticles (B-NP) and bevacizumab-loaded HSA nanoparticles coated with PEG35 (B-NP-PEG35) were administered. A single dose of 5 mg of bevacizumab/kg of body weight was administered intravenously and pictures were taken every two hours up to ten hours after administration.

Figure 13:
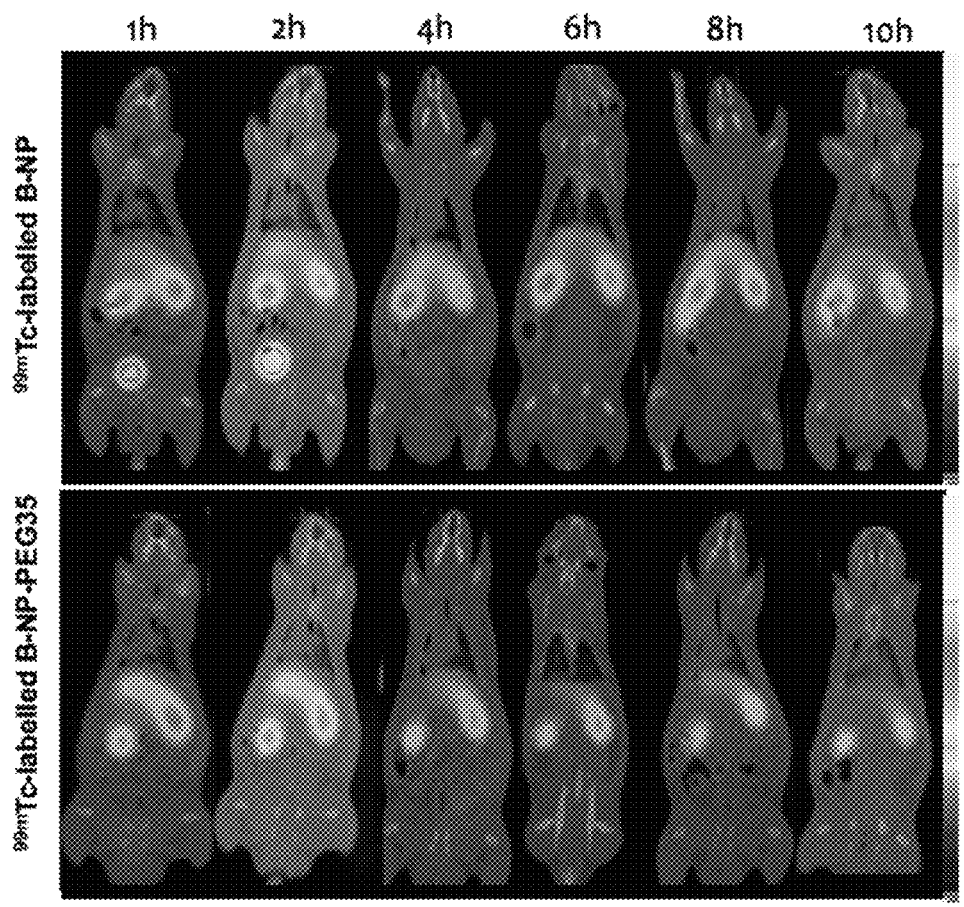
FIG. 13. In vivo SPECT-CT images of $^{99m}$Tc-labelled B-NP (upper row) compared with $^{99m}$Tc-labelled B-NP-PEG35 (bottom row) after intravenous administration to Wistar rats. Images in each row correspond to the same animal studied at the time points indicated in the figure.

An hour after the intravenous administration radioactivity associated with the injection of B-NP and B-NP-PEG35 is observed in liver and kidneys as can be seen in FIG. 13. Also it is worth notice that there is less hepatic uptake of B-NP-PEG35. B-NP and B-NP-PEG35 does not accumulate in any organ.

Example 11. Effect of Bevacizumab-Loaded Albumin Nanoparticles on Corneal Neovascularization Male Wistar rats of approximately 200 g were obtained from Harlan in order to test the efficacy of bevacizumab-loaded nanoparticles in a rat model of corneal neovascularization. Studies were approved by the Ethical Committee for Animal Experimentation of the Institution (protocol number 172-14) in accordance with the European legislation on animal experiments.

Animals were maintained under sedation after intraperitoneal administration of 100 μl of a 5 mg/kg xylacine solution (Xilagesic, Calier Laboratory) and 200 µl of a 40 mg/kg ketamine solution (IMALGENE, Merial). Then, one drop of a cycloplegic collyrium (Coliricusi Tropicamida, 10 mg/ml, Alcon) was administered to each eye of rats. After 5 minutes, the corneas of rats were burned by applying a silver nitrate stick (Argepenal, Braun) on the surface of the eyes for 5 seconds. Finally, the eyes were washed with a sterile solution of NaCl 0.9% p/v.

Twelve hours later, animals were anaesthetized with isofluorane (Isovet, Spain) and divided in different groups. The following treatments were applied as eye drops in the eyes of animals: (i) 10 µl aqueous solution of 4 mg/ml bevacizumab (Avastin®) every 12 hours during 7 days, (ii) 10 µl of an aqueous solution 4 mg/mL of aflibercept (Eylea®) every 12 hours during 7 days, (iii) 10 µl of an aqueous solution 0.1% of dexamethasone phosphate (Coliriculi Dexametasona®) every 12 hours during 7 days (iv) bevacizumab-loaded albumin nanoparticles (B-NP; 10 µL suspension containing 40 g bevacizumab) every day during one week, and (v) bevacizumab-loaded albumin nanoparticles coated with PEG35 (B-NP-PEG35; 10 µL suspension containing 40 µg bevacizumab) every day during 1 week. As controls, a group of animals received physiological serum (PBS) and another group of animals received human serum albumin dissolved in PBS (HSA) in a similar amount to that administered with B-NP-PEG35.

Figure 14:
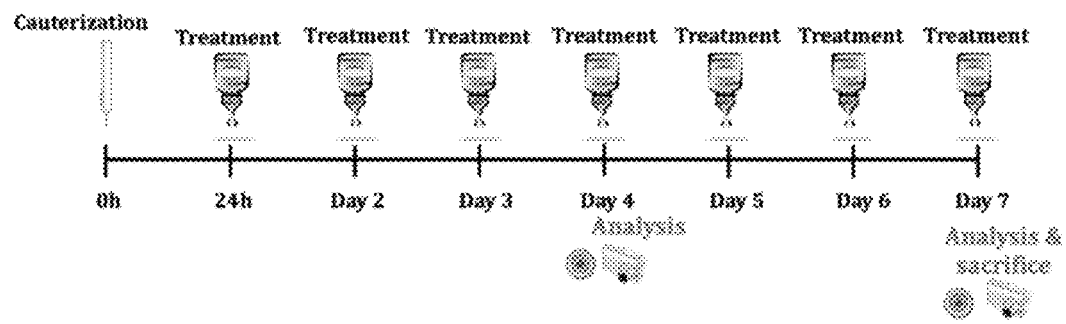
FIG. 14. Schematic of the timeline showing cauterization of the cornea occurring at 0 h (Day 0) and the first treatment at 24 h (Day 1).

FIG. 14 corresponds to the schematic timeline showing cauterization of the cornea occurring at 0 h (Day 0) and the first treatment at 24 h (Day 1).

For calculations, digital images of the corneas were taken and analysed using ImageJ software (public domain, http://rsb.info.nih.gov/ij/). The images were analyzed in binary mode, turning the images to a black-and-white format. From these images, the total area of the cornea was determined as well as the surface of the cornea occupied by the burn with silver nitrate (lesion) and the area affected by the generation of new vessels (corneal neovascularization) were calculated by pixel counting. From these parameters, the invasive area (IA) and the CNV (corneal neovascularization normalized by the lesion surface) were determined as follows:

IA=[(area affected by the genesis of new vessels)/
(total corneal area)]×100

CNV=IA/(surface of the eye affected by the burn)

Figure 15:
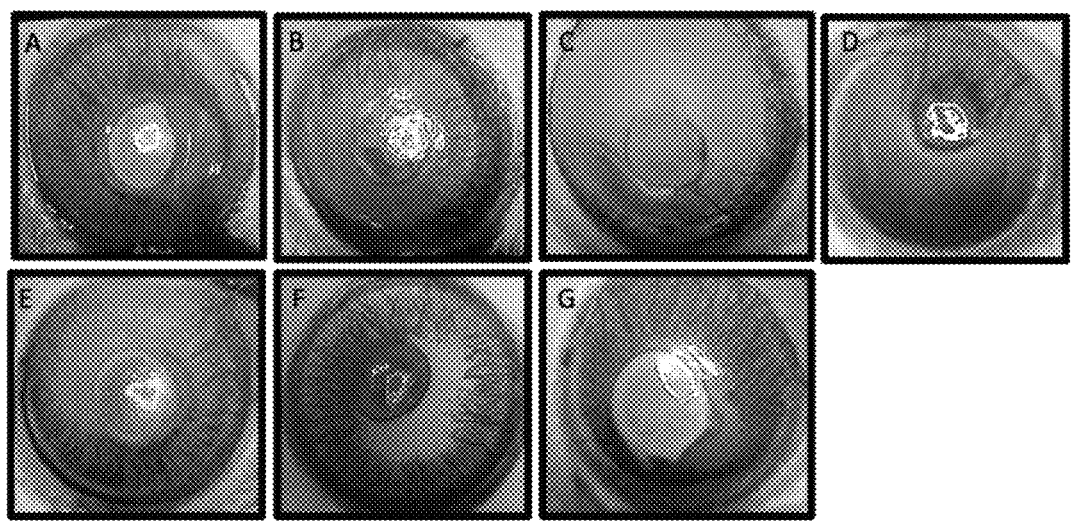
FIG. 15. Photographs of the corneas of animals treated with: (A) physiological serum [Control (−)]; (B) Avastin® (4 mg/mL bevacizumab); (C) albumin nanoparticles loaded with bevacizumab (B-NP); (D) albumin nanoparticles loaded with bevacizumab coated with PEG 35,000 (B-NP-PEG35); (E): human serum albumin solution (HSA); (F): Eylea® (EYLEA); (G): dexamethasone (DEXA).
Figure 16:
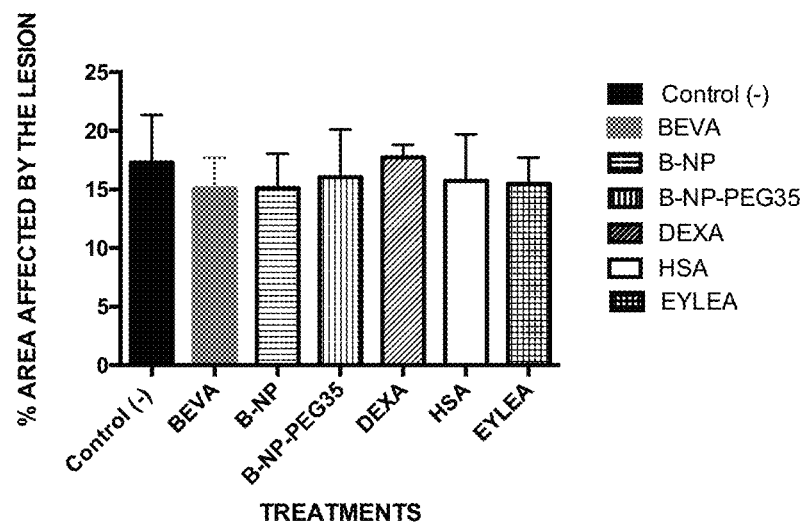
FIG. 16. Lesion area expressed as a percentage of corneal area affected by the burn. No statistical significant differences were found amongst the lesions of the different groups. The data are shown as the mean±SD (n=9).

Table 5 summarizes the efficacy of the different bevacizumab treatments as a result of the reduction in the eye surface affected by the neovascularization induced by the lesion (FIG. 15). In all cases, the lesion induced in the eyes of animals was similar and no statistical differences were found on the lesion areas between the four groups (p>0.05; FIG. 16).

Figure 17:
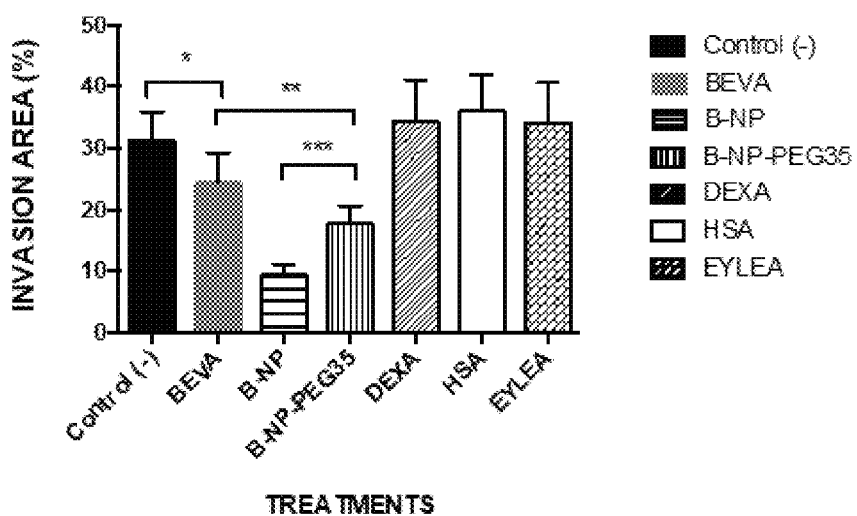
FIG. 17. Invasion area (IA), fraction of corneal area in which vessels are present. The data are shown as the mean±SD (n=9).
*p<0.01 ANOVA followed by Tukey test significantly different from Control (−)
**p<0.01 ANOVA followed by Tukey test significantly different from BEVA

The group of animals treated with the solution of bevacizumab (BEVA) showed a lower surface of the eye affected by neovascularization than animals receiving PBS (negative control). On the other hand, in animals treated with bevacizumab-loaded nanoparticles (B-NP), the surface of the eye affected by corneal neovascularization was found to be 2.7 times lower than for animals treated with Avastin® (BEVA) (FIGS. 17 and 18). When animals were treated with bevacizumab-loaded in pegylated a nanoparticle, the decrease in the surface affected by the neovascularization was about 1.4 times lower than in animals treated with Avastin®. It is important to highlight that animals treated with nanoparticles received 50% less of bevacizumab administered to animals treated with Avastin®. Another important observation was that, under our experimental conditions, neither dexamethasone nor Eylea® demonstrated a positive effect on the neovascularization (Table 9, FIG. 15).

TABLE 5

Effect of bevacizumab formulations on the corneal neovascularization induced by the burn with a silver nitrate stick. BEVA: Bevacizumab solution (Avastin ®, 4 mg/mL, two doses per day during 7 days); B-NP: bevacizumab-loaded albumin nanoparticles (4 mg/mL, one dose per day during 7 days); B-NP-PEG35: bevacizumab-loaded albumin nanoparticles coated with PEG35 (4 mg/mL, one dose per day during 7 days); HSA: human serum albumin solution; Dexamethasone: 0.1% solution twice per day during 7 days; Eylea: Aflibercept solution (Eylea ®, 4 mg/mL, two doses per day during 7 days); Control: PBS. IA: invasion area. CNV: corneal neovascularization normalized by the lesion surface. Data expressed as mean +/− SD of n = 9.

| | Surface of the eye affected by lesion (%) | IA (%) | CNV (%) |
|---|---|---|---|
| Control (−) | 17.3 ± 4.0$^a$ | 31.3 ± 4.6$^a$ | 1.89 ± 0.49$^a$ |
| BEVA | 15.1 ± 2.6$^a$ | 24.4 ± 4.7$^a$ | 1.69 ± 0.53$^a$ |
| B-NP | 15.1 ± 2.9$^a$ | 9.4 ± 1.6$^e$ | 0.74 ± 0.24$^d$ |
| B-NP-PEG35 | 16.0 ± 4.1$^a$ | 17.7 ± 2.9$^d$ | 1.18 ± 0.38$^b$ |
| HSA | 15.7 ± 3.9$^a$ | 36.0 ± 5.9$^a$ | 2.41 ± 0.60$^a$ |
| Dexamethasone | 17.7 ± 1.1$^a$ | 34.4 ± 6.7$^a$ | 1.94 ± 0.35$^a$ |
| Eylea | 15.5 ± 2.2$^a$ | 34.1 ± 6.5$^a$ | 2.27 ± 0.68$^a$ |

$^b$p < 0.05 ANOVA followed by Tukey test significantly different from Control (−)
$^c$p < 0.01 ANOVA followed by Tukey test significantly different from Control (−)
$^d$p < 0.005 ANOVA followed by Tukey test significantly different from Control (−)
$^e$p < 0.001 ANOVA followed by Tukey test significantly different from Control (−)

Histology

For histological study of the eyes with corneal neovascularization, at the end of the treatment, 2 eyes of each group were enucleated. The ocular surface was washed with saline and the anterior pole was separated from the posterior one. Corneas were flat-mounted, fixed with 4% paraformaldehyde for 24 h and then several washes were performed on each sample with PBS. The corneas were kept in methanol 70% for posterior cutting and analysis.

For the analysis of the corneas, these were included in paraffin and 4 micrometers sections were sliced from the center of the cornea and the neovascularization area. Then they were stained with haematoxylin-eosin and analyzed using light microscopy. The evaluation of the sections included the intensity of neovascularization, the intensity of inflammation, fibrosis, edema and average thickness of the cornea. The study was performed by an examiner blind to the treatment groups. Images were taken with a Nikon Eclipse Ci microscope equipped with a digital camera Nikon DS-Ri 1. The images were analyzed using the calibrated analysis system for digital images Nikon's NIS-elements.

For the evaluation of the intensity of neovascularization, the following score was used: 0=absence of neovascularization; 1=minimal or close to negative vascularization; 2=mild vascularization; 3=limited or focal vascularization in the subepithelial and prestromal areas (moderate neovascularization); 4=very frequent or intense; 5=diffuse and intense vascularization. In a similar way, the intensity of inflammation was scored as follows: 0=absence of inflammation; 1=minimal or close to negative inflammation; 2=focal, low count of mixed inflammatory cell types such as lymphocytes, neutrophil leukocytes, and eosinophil leukocytes); 3=moderate inflammation; 4=very frequent or intense; 5=intense, diffuse, mixed inflammatory cell types. The scaling system for the fibroblast activity was: 0=absence of fibroblast activity; 1=minimal or close to negative fibroblast activity; 2=focal fibroblast activity; 3=moderate fibroblast activity; 4=very frequent; 5=diffuse and intense fibroblast activity. Finally, the oedema was classified with the following score: 0=absence of oedema; 1=minimal or close to negative oedema; 2=mild oedema; 3=moderate oedema; 4=very frequent or intense; 5=diffuse and intense oedema.

Figure 19:
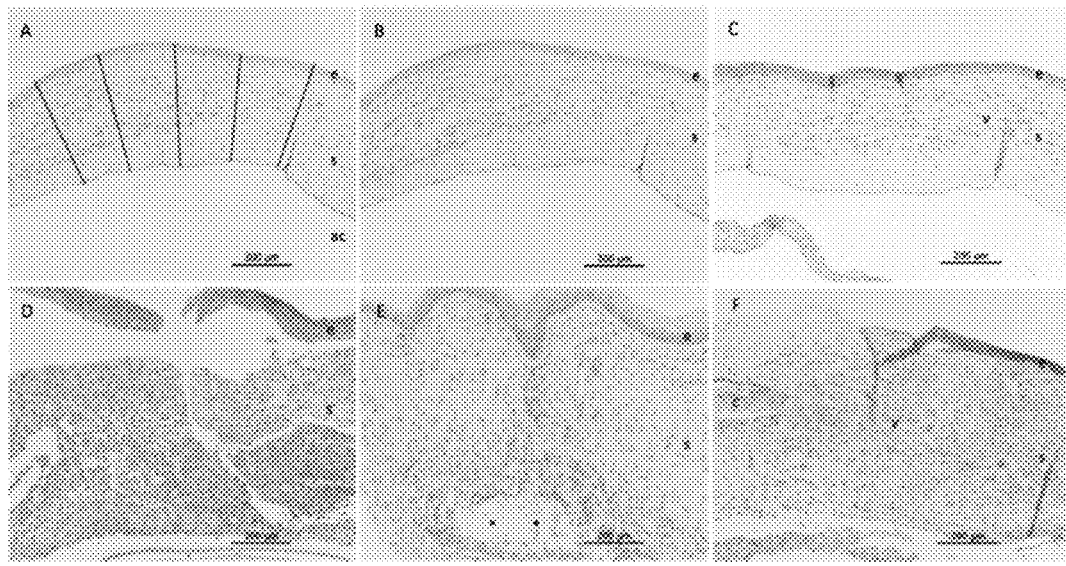

FIG. 19 shows the histological studies of eyes of animals involved in the study. The lesions on corneas treated with B-NP (FIG. 19B) and B-NP-PEG35 (FIG. 19C) are in recovery phase and although before they were affecting the vision temporarily now is not. Therefore the damage is reversible. On the contrary, the lesions on corneas treated with physiological serum are very serious affecting the vision and appeared to be irreversible (FIG. 19F).

TABLE 6

Histopathological evaluations of samples obtained from eyes of animals. Control-: animals treated with physiological serum; BEVA: animals treated with Avastin ®; B-NP: animals treated with bevacizumab-loaded nanoparticles; B-NP-PEG35: animals treated with bevacizumab-loaded pegylated nanoparticles.

| Sample | Fibrosis | Inflammation | Average Thickness (μm) | Vascularization | Oedema |
|---|---|---|---|---|---|
| Control | 4 | 4 | 774.7 | 4 | 3 |
| BEVA | 1 | 4 | 570.5 | 2 | 1 |
| B-NP | 1 | 2 | 287.7 | 1 | 0 |
| B-NP-PEG35 | 1 | 2 | 430.9 | 4 | 1 |

Table 6 summarizes the hispopathological evaluations in the different groups. The corneas treated with serum showed a thickness 1.4 times higher than the ones treated with bevacizumab and 2.7 times higher than those treated with B-NP. On the other hand, corneas treated with Avastin® (BEVA) presented a thickness 2 times higher than the corneas treated with B-NP and 1.3 times more than those treated with B-NP-PEG35. In a similar way, corneas treated with B-NP displayed the best symptoms with a low fibrosis degree, low vascularization and absence of edema.

Example 12. Biodistribution of Nanoparticles after Intravenous Administration to Tumour Bearing Nude Mice For tumor imaging experiments in mice, human hepatocarcinoma cells (HepG2) were cultured in standard conditions, harvested one week after plating and suspended in PBS. Tumours were induced in nude mice after subcutaneous injection of $5\times10^5$ HepG2 cells in two different locations: the right limb and the upper part of the back. Tumour growth was followed for 12-15 days until clearly visible and then animals were used for SPECT-CT in vivo imaging experiments after intravenous injection of $^{99m}$Tc labelled HSA nanoparticles coated with PEG35 (NP-PEG35). One and 4 hours after i.v. administration, animals were euthanized, and both tumours and a portion of muscle from the contralateral leg (without tumour) excised. Samples were counted in a gamma counter calibrated for $^{99m}$Tc, corrected for sample weight and decay and tumour/non tumour ratio calculated using the muscle from the contralateral leg as background.

In tumor bearing mice, radioactivity associated with intravenously injected NP-PEG35 is concentrated in the tumors (if compared with normal tissue) as can be seen in FIG. 20. Such phenomenon seems to be time-dependent, as 4 hours after administration of the nanoparticles the amount present in the tumors is decreased, albeit it already remains in high values (ratio tumor/non-tumor>6).

Example 13. Effect of Bevacizumab-Loaded Albumin Nanoparticles on a Murine Colorectal Cancer Model Studies were approved by the Ethical Committee for Animal Experimentation of the Institution (protocol number 107-16) in accordance with the European legislation on animal experiments. For the experiments forty-two male athimic nude mice of around 20 grams and 3 weeks of age were purchased from Harlan Sprague Dawley, Inc. Mice were kept in a controlled environment in accordance with institutional guidelines. Food and water were supplied ad libitum.

Human colon cancer cells (HT-29) were cultured in standard conditions, harvested one week after plating and suspended in PBS. For the tumor induction mice were anesthetized with isoflurane by inhalation and 100 uL containing $2-3\times10^6$ of HT-29 tumor cells (bevacizumab-sensitive human colon cancer cell line) were injected subcutaneously in the right lateral flank of each animal. Tumour growth was followed for 12-15 days until clearly visible (diameter 0.4-0.6 cm) and then treatment was started.

Mice were randomized into six groups of 7 animals each one: (i) aqueous solution of bevacizumab (Avastin), (ii) bevacizumab-loaded albumin nanoparticles (B-NP), (iii) bevacizumab-loaded albumin nanoparticles coated with PEG35,000 (B-NP-PEG35), (iv) physiological serum (PBS), (v) empty nanoparticles coated with PEG35,000 (NP-PEG35) in a similar amount to that administered with B-NP-PEG35 and (vi) an aqueous solution of HSA containing similar amount of albumin than the group that received B-NP. In all cases, 150-200 μl of the preparations containing 5 mg of bevacizumab/kg of body weight was administered twice/week intravenously. The control group received an intravenously injection with 0.9% saline at the same time points.

Blood samples were taken at day 0 (before the first administration), at day 15, day 22 and day 26 after the first administration. Bevacizumab serum concentration was measured by a specific enzyme immunoassay (Shikari Q-Beva).

The tumor volume and weights were recorded 1-2 times/week. Tumors (V) were measured in two dimensions, width (W) and length (L) with a caliper and calculated using the following equation (eq. 5):

$$V(mm^3) = length \times (width)^2 \times 0.5 \quad [\text{eq. 5}]$$

FIG. 21 shows the tumor volume versus time. A tumor with identical volume was grown in each group and no statistical differences were found on the tumor volume between the six groups at the beginning of the experiment (p>0.05).

At day 12 the group receiving B-NP-PEG35 showed a tumor volume significantly lower (p<0.05) than the rest of groups. By the day 14, the groups that received BEVA and B-NP-PEG35 presented a tumor volume significantly lower (p<0.05) than the rest of groups. At day 22, the groups that did not receive any treatment showed a higher tumor volume than the animals treated with bevacizumab-loaded nanoparticles (B-NP) bevacizumab (BEVA) and with bevacizumab-loaded in pegylated nanoparticles (B-NP-PEG35). It is worth mentioning that, by the end of the experiment, half of the animals in the group that did not receive bevacizumab developed ulcers in the tumors.

FIG. 22 shows the bevacizumab levels in serum. Samples were taken at days: 0 (before the administrations), 15, 22 and 26 after the first administration. It is worth noting that there is an increase of serum bevacizumab levels at day 22 that corresponds to the day after one of the weekly administration. It can be seen in FIG. 22 that the serum levels of bevacizumab in those mice receiving the free drug are up to 6 times higher than the ones receiving the nanoparticles (B-NP and B-NP-PEG35).

The benefits of the administration of bevacizumab encapsulated into nanoparticles lie in lower serum levels of bevacizumab. After intravenous administration of free bevacizumab there is a high concentration of the drug in the bloodstream, which may cause side effects. This concentration decreases slowly to reach a plateau. However, after the administration of a new dose, the bevacizumab concentration in the bloodstream increases (see FIG. 22) thereby increasing the probability of side effects.

On the other hand, after the intravenous administration of bevacizumab nanoparticles the serum levels of the drug increase slowly to reach a plateau. This concentration is six times lower than the one obtained with free bevacizumab, which remains constant. Also, every time a new dose is administered the peak concentration of bevacizumab in the blood is much lower. This decreases the likelihood of side effects.

Also polyethylenglycol imparts a steric barrier to the surface of nanoparticles preventing the opsonization, which is the, main mechanism for the loss of the injected dose (ID) within a few hours after i.v. injection.

Pet Imaging

At the end of the experiment, 3 mice of bevacizumab and bevacizumab-loaded in pegylated nanoparticles treatment, and of the physiological serum were selected to undergo a $^{18}$F-FDG-PET imaging. For that, mice were fasted overnight but allowed to drink water ad libitum. The day after, mice were anaesthetized with Isoflurane 2% in 100% $O_2$ gas and kept still during the $^{18}$F-FDG PET. Forty minutes before scanning, $^{18}$F-FDG (10 MBq±2 in 80-100 µL) was injected via the tail vein. PET imaging was performed in a dedicated small animal Philips Mosaic tomograph (Cleveland, Ohio), with 2 mm resolution, 11.9 cm axial field of view (FOV) and 12.8 cm transaxial FOV. Anesthetized mice were placed horizontally on the PET scanner bed to perform a static acquisition (sinogram) of 15 min. Images were reconstructed using the 3D Ramla algorithm (a true 3D reconstruction) with 2 iterations and a relaxation parameter of 0.024 into a 128×128 matrix with a 1 mm voxel size applying dead time, decay, random and scattering corrections. For the assessment of tumor $^{18}$F-FDG uptake, all studies were exported and analysed using the PMOD software (PMOD Technologies Ltd., Adliswil, Switzerland). Regions of interest (ROIs) were drawn on coronal 1-mm-thick small-animal PET images on consecutive slices including the entire tumor. Finally, maximum standardized uptake value (SUV) was calculated for each tumor using the formula:

$$SUV=[\text{tissue activity concentration (Bq/cm}^3\text{)/injected dose (Bq)}]\times\text{body weight (g)}$$

Table 7 summarizes the PET Imaging results in the different groups. Regarding to the SUVmax (maximum tumor uptake) the lowest value corresponded to the group treated with B-NP-PEG35, while the highest one corresponded to the group that received physiological serum.

In terms of the volume, the lowest values belonged to the groups treated with B-NP-PEG35 and HSA. However, the animals selected of the HSA group were not representative because they were the only ones that did not present ulcers. The highest value belonged again to the group that did not receive any treatment (physiological serum). The B-NP-PEG35 group presented a volume 3 times smaller than the physiological serum group and 1.5 times smaller than the BEVA group.

Finally, the TLG (total lesion glycolysis) showed the smallest value for the group treated with B-NP-PEG35, that it was 1.5 times lower than the group treated with BEVA and up to 3.5 times lower than the group receiving physiological serum.

TABLE 7

PET Imaging results. P.S.: animals treated with physiological serum; B-NP-PEG35: animals treated with bevacizumab-loaded pegylated nanoparticles; BEVA:animals treated with Avastin ®.

| | SUV max | Volume | TLG |
|---|---|---|---|
| P.S. | 1.35 | 0.91 | 0.77 |
| B-NP-PEG35 | 0.97 | 0.33 | 0.22 |
| BEVA | 1.15 | 0.48 | 0.34 |

Example 14. Preparation of Ranibizumab-Loaded Human Serum Albumin Nanoparticles

Ranibizumab-loaded HSA nanoparticles were prepared following the same procedure as that described in Example 1 for bevacizumab-loaded albumin nanoparticles.

For the ranibizumab-loaded nanoparticles the optimum antibody/albumin ratio was 0.15. The ranibizumab-nanoparticles displayed a particle size of approximately 210 nm with a PDI lower than 0.3 and a zeta potential of −15 mV.

The invention claimed is:

1. A pharmaceutical composition comprising:
    a plurality of nanoparticles, said nanoparticles comprising a solid core comprising a non-crosslinked albumin matrix and a monoclonal antibody and wherein the monoclonal antibody is distributed throughout the albumin matrix, said solid core being optionally coated with a non-ionic polymer; and
    a pharmaceutically acceptable excipient, carrier or vehicle, wherein when said solid core is coated, it is coated with a non-ionic polymer.

2. The pharmaceutical composition according to claim 1, wherein the nanoparticles are in the form of a dry powder.

3. The pharmaceutical composition according to claim 1, wherein the pharmaceutically acceptable excipient, carrier or vehicle is suitable for oral, topical or parenteral administration.

4. The pharmaceutical composition according to claim 1, wherein the albumin is human serum albumin or bovine serum albumin.

5. The pharmaceutical composition according to claim 1, wherein the monoclonal antibody is selected from the group consisting of bevacizumab, ranibizumab, trastuzumab, cetuximab and rituximab.

6. The pharmaceutical composition according to claim 1, wherein the non-ionic polymer is selected from the group consisting of hydroxyethylcellulose, hydroxy-n-propylcellulose, hydroxy-n-butylcellulose, hydroxypropylmethyl cellulose, hydroxypropylmethyl cellulose phthalate, ethylhydroxyethylcellulose, starch, dextran, polyvinylpyrrolidone, Eudragit® S-100 (poly(methacrylic acid, methyl methacrylate) 1:2), Eudragit® NM (poly(ethyl acrylate, methyl methacrylate) 2:1), Eudragit® NE (poly(ethyl acrylate, methyl methacrylate) 2:1), and a polyalkylene glycol.

7. A method of treating ocular diseases or cancer, which method comprises administering to a patient in need of such a treatment a therapeutically effective amount of nanoparticles, wherein said nanoparticles comprise a solid core, said solid core comprising a non-crosslinked albumin matrix and a monoclonal antibody having affinity for at least one target within the ocular tissue or within a cancerous tissue, and wherein the monoclonal antibody is distributed throughout the albumin matrix, said solid core being optionally coated with a non-ionic polymer, wherein when said solid core is coated, it is coated with a non-ionic polymer.

8. The method according to claim 7, wherein the monoclonal antibody/albumin weight ratio ranges from 0.01 to 0.5.

9. The method according to claim 7, wherein the non-ionic polymer/albumin ratio ranges from 0.02 to 5 (w/w).

10. The method according to claim 7, wherein the albumin is human serum albumin or bovine serum albumin.

11. The method according to claim 7, wherein the monoclonal antibody is selected from the group consisting of bevacizumab, ranibizumab, trastuzumab, cetuximab and rituximab.

12. The method according to claim 7, wherein the non-ionic polymer is selected from the group consisting of hydroxyethylcellulose, hydroxy-n-propylcellulose, hydroxy-n-butylcellulose, hydroxypropylmethyl cellulose, hydroxypropylmethyl cellulose phthalate, ethylhydroxyethylcellulose, starch, dextran, polyvinylpyrrolidone, Eudragit® S-100 (poly(methacrylic acid, methyl methacrylate) 1:2), Eudragit® NM (poly(ethyl acrylate, methyl methacrylate) 2:1), Eudragit® NE (poly(ethyl acrylate, methyl methacrylate) 2:1), and a polyalkylene glycol.

13. The method according to claim 7, wherein said nanoparticles are obtainable by a method comprising:
a) preparing an aqueous solution of albumin and a monoclonal antibody having affinity for at least one target within the ocular tissue or within a cancerous tissue;
b) titrating the aqueous solution of step a) to a pH between 4 and 5;
c) adding a desolvating agent to the aqueous solution of step b) to form albumin-monoclonal antibody nanoparticles;
d) optionally, incubating the albumin-monoclonal antibody nanoparticles formed in step c) with a non-ionic polymer; and
e) optionally, drying the nanoparticles by vacuum drying, spray drying or by freeze-drying.

14. The method according to claim 7, wherein said monoclonal antibody is selected from an anti-VEGF or anti-VEGF R2 antibody.

15. The method according to claim 7, wherein
said antibody is an anti-VEGF antibody and the cancer is breast cancer, lung cancer, pancreatic cancer, multiple myeloma, renal cell carcinoma, prostate cancer, melanoma, colon cancer, colorectal cancer, kidney cancer, cervical cancer, ovarian cancer, liver, renal and gastric cancer, bladder cancer or squamous cell cancer;
said antibody is trastuzumab and the cancer is breast cancer, lung cancer, pancreatic cancer, multiple myeloma, renal cell carcinoma, prostate cancer, melanoma, colon cancer, colorectal cancer, kidney cancer, cervical cancer, ovarian cancer, liver, renal and gastric cancer, bladder cancer or squamous cell cancer;
said antibody is cetuximab and the cancer is lung cancer, renal cell carcinoma, colorectal cancer, cervical cancer, ovarian cancer or squamous cell cancer; or
said antibody is rituximab and the cancer is lymphoma or leukemia.

16. A nanoparticle comprising a solid core, said solid core comprising a non-crosslinked albumin matrix and a monoclonal antibody and wherein the monoclonal antibody is distributed throughout the albumin matrix, said solid core being coated with a non-ionic polymer.

17. The method according to claim 14, wherein the ocular disease is selected from macular degeneration, corneal neovascularization or angiogenesis, iris neovascularization or angiogenesis, retinal neovascularization or angiogenesis, diabetic proliferative retinopathy, non-diabetic proliferative retinopathy, glaucoma, infective conjunctivitis, allergic conjunctivitis, ulcerative keratitis, non-ulcerative keratitis, episcleritis, scleritis, diabetic retinopathy, uveitis, endophthalmitis, ocular infectious conditions or ocular inflammatory conditions.

18. The method according to claim 7, wherein the monoclonal antibody is homogeneously distributed throughout the albumin matrix.

19. The pharmaceutical composition according to claim 1, wherein the monoclonal antibody is homogeneously distributed throughout the albumin matrix.

* * * * *

UNITED STATES PATENT AND TRADEMARK OFFICE
CERTIFICATE OF CORRECTION

| | |
|---|---|
| PATENT NO. | : 10,993,994 B2 |
| APPLICATION NO. | : 16/625040 |
| DATED | : May 4, 2021 |
| INVENTOR(S) | : Daniel Alberto Allemandi et al. |

It is certified that error appears in the above-identified patent and that said Letters Patent is hereby corrected as shown below:

On the Title Page

Item (71), UNIVERSIDAD DE NAVARRA, Navarra (ES); CONSEJO NACIONAL DE INVESTIGACIONES CIENTÍFCAS Y TÉCNICAS, Ciudad Autónoma de Buenos Aires (AR); UNIVERSIDAD NACIONAL DE CÓRDOBA, Córdoba (AR)

CORRECTION: UNIVERSIDAD DE NAVARRA, Navarra (ES); CONSEJO NACIONAL DE INVESTIGACIONES CIENTÍFICAS Y TÉCNICAS, Ciudad Autónoma de Buenos Aires (AR); UNIVERSIDAD NACIONAL DE CÓRDOBA, Córdoba (AR)

Item (72), Daniel Alberto Allemandi, Córdoba (AR); Carolina Boiero, Córdoba (AR); Juan Manuel Irache Garreta, Navarra (ES); Juan Manuel Llabot, Cordova (AR); Inés Luis De Redíin Subirá, Navarra (ES); Iván Peñuelas Sánchez, Navarra (ES); Gemma Quincoces Fernández, Navarra (ES)

CORRECTION: Daniel Alberto Allemandi, Córdoba (AR); Carolina Boiero, Córdoba (AR); Juan Manuel Irache Garreta, Navarra (ES); Juan Manuel Llabot, Córdoba (AR); Inés Luis De Redín Subirá, Navarra (ES); Iván Peñuelas Sánchez, Navarra (ES); Gemma Quincoces Fernández, Navarra (ES)

Signed and Sealed this
Tenth Day of May, 2022

Katherine Kelly Vidal
*Director of the United States Patent and Trademark Office*